US006409990B1

(12) United States Patent
Vera

(10) Patent No.: US 6,409,990 B1
(45) Date of Patent: Jun. 25, 2002

(54) MACROMOLECULAR CARRIER FOR DRUG AND DIAGNOSTIC AGENT DELIVERY

(75) Inventor: David R. Vera, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/569,466

(22) Filed: May 12, 2000

Related U.S. Application Data

(60) Provisional application No. 60/134,329, filed on May 14, 1999.

(51) Int. Cl.$^7$ .................. A61B 5/0555; A61K 49/00; A61K 49/04; A61K 31/715; A01N 43/04
(52) U.S. Cl. .................. 424/9.35; 424/9.1; 424/9.3; 424/9.351; 424/9.4; 424/9.43; 514/54; 514/58
(58) Field of Search ................. 424/9.35, 9.3, 424/9.4, 9.43, 9.1, 9.351; 514/58, 54

(56) References Cited

U.S. PATENT DOCUMENTS

| | | | | |
|---|---|---|---|---|
| 4,707,440 A | * | 11/1987 | Stavrianopoulos | 435/6 |
| 4,822,594 A | | 4/1989 | Gibby | |
| 5,175,269 A | * | 12/1992 | Stavrianopoulos | 536/26.13 |
| 5,336,762 A | | 8/1994 | Ranney | |
| 5,490,991 A | * | 2/1996 | Enriquez et al. | 424/488 |
| 6,051,207 A | * | 4/2000 | Klaveness et al. | 424/9.1 |

FOREIGN PATENT DOCUMENTS

| | | |
|---|---|---|
| CS | 263561 | 9/1988 |
| DE | 286598 A5 | 1/1991 |
| EP | 0186947 | 10/1985 |
| WO | WO 97/25139 | 7/1997 |
| WO | WO 98/23293 | 6/1998 |

OTHER PUBLICATIONS

Armitage, F. E. et al, "Polymeric Contrast Agents for Magnetic Resonance Imaging: Synthesis and Characterization of Gadolinium Diethylenetriaminepentaacetic Acid Conjugated to Polysaccharides." *Bioconjugate Chemistry.* 1(6):365–74, 1990.

Dubois, M. et al., "Colorimetric Method for Determination of Sugars and Related Substances." *Analytical Chemistry.* 28(3):350–6, 1956.

Fields, R., "The Rapid Determination of Amino Groups with TNBS" Modification Reactions 38:464–8.

Gedda, L. et al, "Development and in Vitro Studies of Epidermal Growth Factor—Dextran Conjugates for Boron Neutron Capture Therapy." *Bioconjugate Chemistry.* 7:584–91, 1996.

Holmberg, A. et al, "Preparation of Sulfhydrylborane—Dextran Conjugates for Boron Neutron Capture Therapy." *Bioconjugate Chemistry.* 4:570–3, 1993.

Krejcarek, G. E. et al, "Covalent Attachment of Chelating Groups to Macromolecules." *Biomedical and Biophysical Research Communications.* 77(2):581–85, 1977.

Krinick, N.L. et al, "Targetable photoactivatable drugs, 2—Synthesis of N-(2-hydroxypropyl)methacrylamide copolymer–anti–Thy 1.2 antibody–chlorine$_6$ conjugates and a preliminary study of their photodynamic effect on mouse splenocytes in vitro." *Macromolecular Chemistry.* 191:839–56, 1990.

Rebizak, R. et al, "Polymeric Conjugates of Gd$^{3+}$–Diethylenetriaminepentaacetic Acid and Dextran. 2. Influence of Spacer Arm Length and Conjugate Molecular Mass on the Paramagnetic Properties and Some Biological Parameters." *Bioconjugate Chemistry.* 9:94–99, 1998.

Rebizak, R. et al, "Polymeric Conjugates of Gd$^{3+}$–Diethylenetriaminepentaacetic Acid and Dextran. 1.Synthesis, Characterization, and Paramagnetic Properties." *Bioconjugate Chemistry.* 8:605–10, 1997.

Sieving, P. F. et al, "Preparation and Characterization of Paramagnetic Polychelates and Their Protein Conjugates." *Bioconjugate Chemistry.* 1:65–71, 1990.

Tomalia, D.A. et al, "A New Class of Polymers: Sunburst–Dendritic Macromolecules." *Polymer Journal.* 17(1):117–32, 1985.

Vera, D.R. et al, "Sentinel Node Imaging Via a Nonparticle Receptor–Binding Radiotracer." *The Journal of Nuclear Medicine.* 38(4):530–5, 1997.

Bhatnagar, A.K. et al. (1997) Renal Imaging with $^{99}$Tc$^m$–dextran. *Nuclear Medicine Comm.* 18:562–66.

Chu, W.–J. and Elgavish, G.A. (1995) Gadolinium and Dysprosium Chelates of DTPA–amide–dextran: Synthesis, $^1$H NMR Relaxivity, and Induced $^{23}$Na NMR Shift. *NMR in Biomedicine* 8:159–163.

Jacobs, R.E. and Fraser, S.E. (1994) Magnetic Resonance Microscopy of Embryonic Cell Linages and Movements. *Science* 263:681–684.

Vera, D.R. et al (19950 A Molecular Receptor–Binding Contrast Agent for Magnetic Resonance Imaging for the Liver. 2:497–506.

Wikström, M. et al. (1992) MR Imaging of Acute Myocardial Infarction in Pigs Using Gd–DTPA–Labeled Dextran. 33:301–308.

\* cited by examiner

*Primary Examiner*—Dameron L. Jones
*Assistant Examiner*—Lauren Q. Wells
(74) *Attorney, Agent, or Firm*—Brown Martin Haller & McClain

(57) ABSTRACT

New macromolecular carriers for drugs and diagnostic agents are described that make use of the chemical attachment of new leashes to oligomeric backbone structures. The synthesis of these leashes and their facile creation, reaction and conjugation with chelators and ligands makes them ideal candidates for use in medicine, and especially diagnostics.

31 Claims, 13 Drawing Sheets

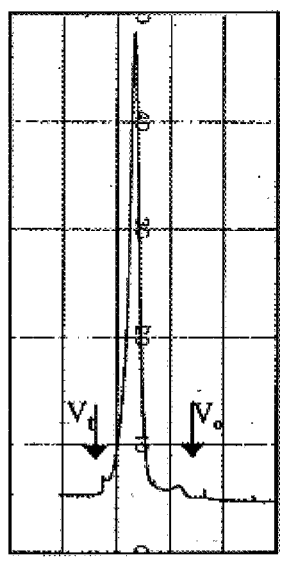
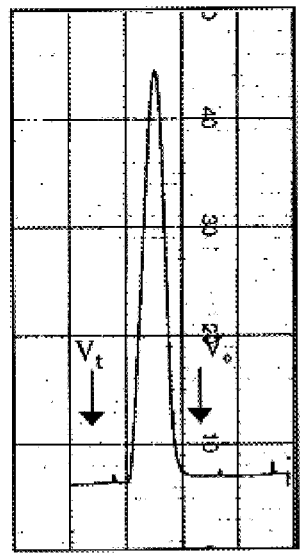
Figure 15a   Figure 15b
Figure 16a   Figure 16b

MACROMOLECULAR CARRIER FOR DRUG AND DIAGNOSTIC AGENT DELIVERY

CROSS-REFERENCES TO RELATED APPLICATIONS

This application claims priority to United States Provisional Patent Application Serial No. 60/134,329, filed May 14, 1999, which is incorporated herein by reference in its entirety including all drawings.

STATEMENT REGARDING FEDERALLY SPONSORED RESEARCH

This application was made possible with assistance provided by NIH grant R01-CA72751. The Federal Government may have rights in the invention.

BACKGROUND OF THE INVENTION

The field of the invention relates to therapeutics and diagnostics that make use of macromolecules as delivery agents.

The use or hypothetical use of certain macromolecules as delivery agents to target appended drugs and diagnostic agents is known, but currently not without severe limitations. Attempts with therapeutics have yielded only limited clinical success due to a lack of inexpensive and nontoxic molecular backbones to which drugs and target substrates of sufficient load can be attached. Similar problems plague current cardiovascular and tumor imaging techniques, which make use of appended agents for magnetic resonance imaging (MRI) and computed tomography (CT).

Focus has thus centered on the delivery agent's molecular backbone, which function is to carry drugs, substrates, and imaging and other diagnostic molecules for delivery to specific cell tissues. The most commonly employed backbones to date are dextran, polylysine, synthetic copolymers, starburst dendrimers, and human serum albumin.

Dextran, a branched polymer of glucose, has an extensive human-use experience, and offers the highest ratio of attachment sites per molecular weight. It is also very hydrophilic, which permits a low injection volume. While dextran is relatively inexpensive, it has the disadvantage of having insufficient chemical flexibility in its usual attachment sites and a high incidence of unwanted cross-linking that results from standard means of attachment.

Polylysine, by contrast, is extremely expensive and has a very limited human-use experience. Despite this, polylysine has the advantage of being available in various chain lengths and the further advantage of its side chains being readily amenable to chemical attachment of drugs and receptor substrates. Consequently, polylysine is frequently employed to test prospective drug delivery systems in animals.

Synthetic copolymers, e.g., as described by Krinick et al., Makromol. Chem. 191:839–856 (1990), offer linearity and a net neutral charge which increases diffusion. Synthetic copolymers offer further advantage in that they may be synthesized in bulk. However, their synthesis requires multiple steps that, if not complex, are nevertheless time consuming, expensive, and therefore inefficient. Further, there is limited human-use experience with synthetic copolymer backgrounds.

Starburst dendrimers (see Tomalia et al. (1985) Polymer J. 17:117–132) are advantageous in that they provide less molecular weight heterogeneity, and therefore more reproducibility and predictability. However, they have the disadvantages that they (1) offer a low, inadequate number of attachment sites per backbone, and (2) have a limited human-use experience. Similar disadvantages characterize the use of human serum albumin.

In light of the foregoing, an inexpensive and nontoxic molecular backbone delivery vehicle replete with high density molecular attachment capabilities is sorely needed.

SUMMARY OF THE INVENTION

It is an object of the invention to remedy or ameliorate one or more of the above-noted problems in the field and to provide useful alternatives.

Specifically, it is an object of the invention to provide a new or improved macromolecule delivery system for agents of any type, diagnostic, therapeutic, or otherwise.

It is a further object of the invention to provide a relatively nontoxic macromolecule possessing a high density of attachment sites relative to what has previously been described in the art.

It is a further object of the invention to improve delivery success and reduce administration volumes in techniques employing macromolecular backbones as delivery vehicles.

It is yet a further object of the invention to provide a macromolecule that is highly available, relatively inexpensive, and of demonstrable value in scientific research and medicine.

It is a further object of the invention to describe the chemical synthesis and product of new chemical attachment leashes having suitable flexibility.

In accordance with one or more of these objectives, in a first aspect the invention features a carrier molecule comprising a backbone, the backbone having affixed thereto a plurality of leash groups having structure $-O(CH_2)_3S(CH_2)_2NH_2$.

In preferred embodiments, the backbone is derived from a polysaccharide, preferably dextran, and the leash structures are accomplished through reaction of an allyl group with aminoethanethiol. When dextran is used, it may be selected from any molecular weight appropriate for the ultimate use of the molecule, its leashes, and conjugates. Different diagnostic and therapeutic applications will call for different MW dextrans, as the person of ordinary skill in the art is aware.

In most advantageous embodiments, it is preferred that at least one chemical group be conjugated to the backbone via the amino groups of the leashes. These chemical groups may be selected from any of a variety of compounds having useful therapeutic or diagnostic uses, including but not limited to: chelators, receptor ligands, lectins, enzymatic substrates, nucleic acids, peptides, polysaccharides, monosaccharides, radiosensitizers, radioprotectors, and dyes. The groups need not be directly useful, but may be indirectly useful by permitting targeting to a given cell or tissue type such that another functional moiety attached to the backbone may perform the affirmative or negative function desired.

The high load and density of leashes per nontoxic backbone is an important aspect of the invention due to the significant kinetic advantages that are obtained for attachment and delivery. Relatively more therapeutic or diagnostic molecules may be delivered to work their purpose. This may include the very simplistic case in which ligands of high density may be simply attached to the backbone molecule such that they more effectively block certain receptors when administered or contacted thereto or therewith. Receptors impart cellular biochemical function. Blockage of that function may have a useful therapeutic value for a given indication and context. Thus, antagonists capable of competitive or noncompetive inhibition with normal or abnormal biological agents are contemplated.

Agonists can also be used to obtain the desired effect in that they may signal or stimulate endocytosis of the backbone moiety and agents to which they are attached, or can signal an intracellular cascade. Those of skill in the art will recognize the broad range of applications and implications for the many embodiments of the invention.

In especially preferred embodiments, the backbone carries both a ligand having a specific affinity for a given tissue or cell type, and a chelator molecule. The chelator normally has nitrogen groups possessing free electrons that adhere tightly to positively charged metal atoms and ions. Preferred chelators for use with the invention include DOTA, MAG3, and DTPA. DOTA is especially preferred because its geometry conveniently and tightly accommodates the gadolinium atom, which can be used for both Computed Tomography (CT) and Magnetic Resonance Imaging (MRI). The MAG3 chelator is preferred for complexation with the radioelement Technetium-99m (Tc-99m), which has a relatively short half-life of 6 hours. This half-life is compatible with biologic processes and clinical protocols, which for sentinel node detection is of sufficient duration to permit a surgeon to evaluate the precise location and extent of, e.g., tumor growth or metastases and remove it. This particular combination thus has excellent application in nuclear medicine.

In other, not necessarily mutually exclusive embodiments, the chelator may be combined with a non-radioisotope or element, e.g., an absorbing element (high density), or paramagnetic atom, each having special application, respectively, in computed tomography and nuclear magnetic or magnetic resonance imaging procedures. These are diagnostic procedures that permit imaging of various physiological or anatomical structures using characteristics of the high density or paramagnetic atoms introduced. Such diagnostic procedures may or may not be used in prelude to therapeutic procedures.

It may further be possible, using embodiments of the invention, to perform both diagnostic and therapeutic procedures at once, e.g., where some of the backbone leashes are conjugated with a diagnosing agent and others are conjugated with a therapeutic agent.

With respect to sentinel node detection, this particular diagnostic procedure takes advantage of high stability, nontoxicity, and high load and affinity supplied by the invention to improve the differentiation, isolation, and excision. This procedure will usually employ a chelator attached to a leash of the invention, to which can be further bound a radioatom such as technetium-99m. Other possibilities for the invention include the use of gadolinium, dysprosium, ytterbium, indium, and other elements possessing useful properties.

To target the above requires the additional use and employment of a receptor substrate, e.g., mannose, galactose, peptides, etc. Use of the term substrate does not necessarily suggest the ability to be acted upon by an enzyme, but can, and preferably does, refer to simple ligand:receptor binding. Thus the term "ligand" may take many forms and constitutions, and may be used synonymously with "receptor substrate" as used herein. Selecting a desired ligand or receptor substrate to target a given receptor is well within the level of skill in the art. Literally thousands of interactions are known which can be exploited for a given application. Furthermore, the targeted receptor may be viral, bacterial, protozoan, fungal, plant, insect, and not necessarily animal or mammalian in origin.

In terms of the degree of allylation, leash attachment, and conjugation, it may be anywhere from 1 to 100%, with 100% preferred. However, where not all leashes are ultimately conjugated, other embodiments may contemplate the addition of a noncharged "blocking" molecule, e.g., a methyl, alkyl, or aryl group to the free amino terminus or termini such that the overall molecule is less charged. In many applications, the less charge the better, as the person of skill is aware.

In a second aspect, the invention features, in addition to the products and applications of the first aspect, methods of producing substantially cross-link-free carrier molecules having a plurality of amino terminated leashes. By "substantially cross-link-free" is meant cross-links introduced by man between molecules of the same type, e.g., glucose units in the same dextran molecule. The term is not meant to embrace the specific, intended conjugation of heteromolecules as described herein to the leashes of the backbone. It is further recognized that backbones, e.g., polysaccharides, may be naturally cross-linked to begin with; the term "substantially cross-link-free" specifically excludes such phenomena.

The term "substantially" is used to acknowledge that certain minimal, artifactual cross-linkages may nevertheless still occur, e.g., through the presence of contaminants or the use of sub-optimum attachment conditions, but that such limited cross-linking is tolerable. In this regard, the term is used to denote that a great object of the invention (to thwart, control or minimize man-made cross-linking phenomena associated with the introduction of conventional leashes to a backbone) is not significantly compromised. As noted, conventional procedures were flawed in this regard, and the invention significantly rectifies this through the use, e.g., of bifunctional groups such as in the preferred embodiment where aminoethanethiol is used. Prior to the invention, it was difficult if not impossible to control these unintended "side reactions", the result of which was to increase molecular weight above, and lower solubility below, tolerable and useful limits.

A preferred method embodiment preferably comprises providing a backbone molecule having a plurality of hydroxyl groups, allylating at least a portion of said hydroxyl groups on said backbone molecule to produce an allyl derivative of said backbone, reacting said allyl groups of said allyl derivative with a compound comprising an amino terminus and a second terminus, said second terminus specifically reactive with said allyl groups of said allyl derivative; and reacting said allyl derivative with said compound to produce a substantially cross-link-free carrier molecule having a plurality of amino terminated leashes.

In preferred embodiments, the backbone is, once again, a polysaccharide, preferably dextran. Preferably, although not necessarily, the compound used to create and affix the leashes to the allyl derivative backbone molecule is aminoethanethiol.

In further method embodiments, conjugation is contemplated as described for the first aspect, e.g., using at least one member selected from the group consisting of chelators, receptor ligands, enzymatic substrates, nucleic acids, peptides, polysaccharides, monosaccharides, radiosensitizers, radioprotectors, and dyes. The dyes can be fluorescent or otherwise distinguishable using visible and/or assistance means common in the art.

Other method embodiments track those already noted for the first aspect.

Still further aspects of the invention are more specific products and product-by-processes. For example, an MRI agent synthesized from the molecule of the first aspect is claimed, as is an MRI agent made according to the methods of the second aspect. Also claimed is a CT agent synthesized from or according to any of the first two aspects. Finally, sentinel node imaging agents are claimed that feature or employ the first or second aspects, and any feasible combination of those aspects' specific embodiments.

BRIEF DESCRIPTION OF THE DRAWINGS

FIG. 15a shows the size distribution of human serum albumin as measured by FPLC. The void (Vo) and total (Vt) volumes of the column are noted.

FIG. 15b shows the size distribution of an embodiment of the invention Dy-DTPA-dextran as measured by FPLC. The void (Vo) and total (Vt) volumes of the column are noted.

FIGS. 16a and 16b are examples of MR blood pool imaging showing images of a tumor-bearing rabbit before (FIG. 16a) and one hour after (FIG. 16b) GdDTPA-dextran injection.

FIG. 19a is a maximum intensity projection image of a healthy rabbit acquired 15 minutes after GdDTPA-dextran (MW=398,000 g/mole, 515 Gd per dextran) injection and FIG. 19b is a similar image of the same animal acquired three hours post-injection.

Figure 1:
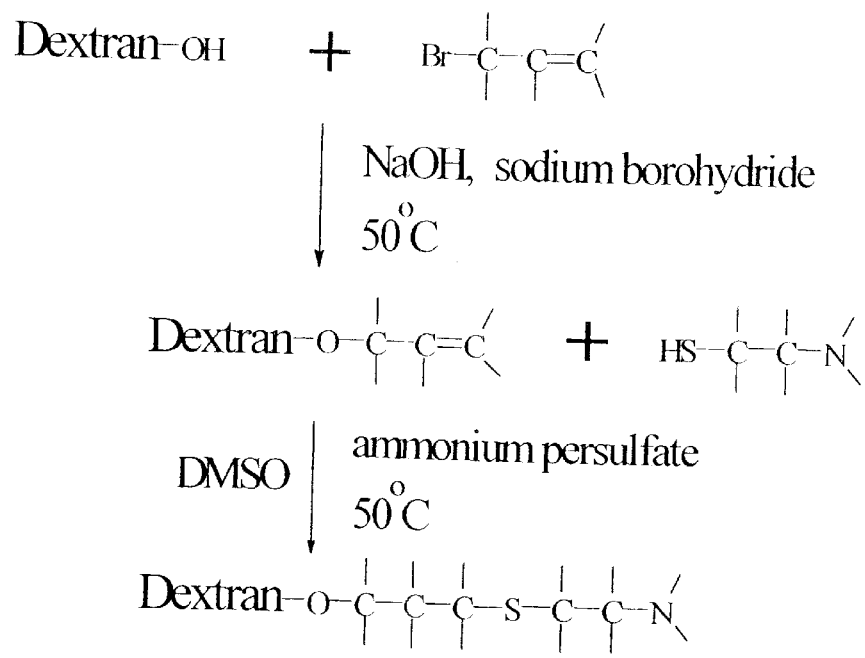
FIG. 1 shows an embodiment of a sequence for covalent coupling of attachment sites to a macromolecular backbone is effected.

The present invention will be better understood from the following detailed description of exemplary embodiments of the invention.

DETAILED DESCRIPTION

The invention pertains to the targeting of drugs and diagnostic agents to specific tissues using a macromolecular delivery vehicle. Before now, there has been only limited clinical success for such vehicles due to lack of inexpensive and nontoxic molecular backbones to which drugs and target substrates can be attached. The invention remedies this by providing new macromolecules produced by novel processes that suppress unwanted cross-linking while preserving nontoxicity, and optimizing leash and load capacity per backbone size.

Although useful when combined or conjugated with therapeutic agents, the invention is especially useful for cardiovascular and/or tumor imaging. A successful cardiovascular and tumor contrast agent for magnetic resonance imaging (MRI) or computed tomography (CT) should possess an inexpensive and nontoxic molecular backbone capable of carrying a high number of contrast substrates. Prior to the invention, this had not been the case.

One embodiment of the invention features a chemical scheme that produces an inexpensive macromolecule with a large number of attachment sites called "leashes". A high number (hundreds) of leashes per backbone molecule permits the attachment of a high density of substrates, drugs, and/or other molecular entities.

An additional useful feature can be found in a preferred embodiment in which the backbone of the macromolecule is dextran. Dextran has an excellent safety record as a cardiovascular volume expander. The extensive human-use of dextran increases the probability that the delivered drug or diagnostic agent will also be nontoxic.

There are many potential uses for the invention, e.g., as pharmaceuticals (i.e., therapeutics) and as diagnostics (i.e., probes). In theory, although most any drug can be used with the invention, the following uses are especially foreseen: attachment of radioprotectors, such as WR2721, (Rasey J S et al. Specific protection of different normal tissues. *Pharmac Ther* 39:33–43, 1988), chemoprotectors, such as Amifostine (Ethyol) (Capizzi R L. Protection of normal tissues from the cytotoxic effects of chemotherapy by amifostine (ethyol): clincial experiences. *Semin Oncol* 21(S11):8–15 (1994)), and radiosenisitizer molecules, such as Misonidazole (Phillips T L. Sensitizers and protectors in clinical oncology. *Semin Oncol* 8:67–82, 1881) and appropriate receptor substrates for tissue specific protection or sensitization; attachment of antiviral drugs and appropriate receptor substrates for tissue-specific antiviral therapy, e.g., to treat hepatitis; attachment of immunomodulators and appropriate receptor substrates or ligands for tissue-specific immunotherapy; attachment of DNA and appropriate receptor substrates for tissue-specific gene therapy, e.g., targeting p52 or suicide genes into cancer cells to induce apoptosis, immunotargeting, etc.; and attachment of peptides and mono- or polysaccharides for targeting to specific receptors. See, e.g., Molteni L (1979), Dextrans as drug carriers. In: Gregoriadis G, ed. *Drug Carriers in Biology and Medicine.* San Diego, Academic Press; 107–125.

In terms of diagnostics, the following uses are especially contemplated: attachment of gadolinium complexes for magnetic resonance imaging (MRI) of the cardiovasculature and/or tumors; attachment of iodinated molecules for computer tomographic (CT) imaging of the cardiovasculature and/or tumors; attachment of ytterbium, dysprosium, or other heavy metal complexes for computer tomographic (CT) imaging of the cardiovasculature and/or tumors; attachment of technetium-99m complexes for scintigraphic imaging of the cardiovasculature and/or tumors; attachment of gadolinium complexes and appropriate receptor substrates for tissue-specific imaging of the liver, lymph nodes, bone marrow, and/or other tissues; attachment of iodinated molecules and appropriate receptor substrates for tissue-specific CT imaging; attachment of ytterbium, dysprosium, or other heavy metal complexes and appropriate receptor substrates for tissue-specific CT imaging; attachment of technetium-99m complexes and appropriate receptor substrates for tissue-specific scintigraphy; and attachment of dyes and fluorescent agents for optical imaging.

Again, the preceding uses are only illustrative of the many possible applications for which the invention can be used. Specific examples for some of these applications follow; other applications will be readily apparent and can be practiced by one of ordinary skill in the art viewing the application.

EXAMPLE 1

Attachment of Leashes to a Molecular Backbone

Dextran, a preferred embodiment for the molecular backbone of the invention, possesses, as do many polysaccharides and branched polysaccharides, a plethora of reactive hydroxyl groups to which chemical attachments can be made. Dextran is a natural product derived from bacteria. It is isolated in high molecular weight form and can be hydrolyzed and purified in controlled fashion to various smaller molecular weight commodities, e.g., molecular weight ("MW") 1,000, 10,000, 40,000, 70,000, 110,000, 150,000 and 500,000. (Amersham Pharmacia Biotech, USA). Each of the listed MW species can be used with the invention and each may have more or less suitable effect for a given application. For example, for tumor imaging one would select a dextran with a size that after conjugation of leashes and reporter groups would yield a final molecular weight within the 50–70 kilodalton (kD) range. This would permit the selective diffusion into tumors, which have greater permeability than normal tissue (see Seymour L W. Passive tumor targeting of soluble macromolecules and drug conjugates. *Critical Reviews of Therapeutic Drug Carrier Systems* 9:135–187 (1992)). Imaging of cardiovascular structures will require conjugates with molecular weights in the 70–100 kD range. The lower limit is set by the desire to minimize renal filtration. The upper limit is set by the increased viscosity of high molecular weight macromolecules, which produces administration problems.

As stated previously, much pharmacological data is available for dextran based on its wide use as a plasma volume expander, in which it has been demonstrated to persist for several weeks after infusion into patients and during which time it is gradually oxidized into smaller forms and cleared via the kidneys. See Goodman and Gilman's *The Pharmacological Basis of Therapeutics*, Eighth Edition, pp. 690–91, Pergamon Press, New York, (1990). The leash attachment was a two-step process, as shown in FIG. 1. The first step is the activation of the dextran hydroxyl units with allylbromine (Holmberg, 1993; Gedda, 1996). This reaction uses 10 grams of PM10 in 75 ml deionized water is carried out at 50° C. and pH 11 (maintained by dropwise addition of 2.5N NaOH) in the presence of sodium hydroxide (2.5 grams) and sodium borohydride (0.2 grams). After 3 hours the solution is neutralized with acetic acid (2.5 M) the reaction is placed in a 5° C. refrigerator for 2 hours, and the top organic layer is decanted. After addition of 100 ml deionized water, the resulting solution is then filtered (5 mm) into an ultrafiltration cell (MWCO=3,000), and dialyzed with 10 exchange volumes of deionized water. The product, allyl-dextran, is concentrated, lyophilized, and stored at −80° C. The mean molecular diameter is measured by laser light scattering (Honeywell MicroTrac UPA 150).

The average number of allyl groups per dextran is calculated in the following manner. The lyophilized allyl-dextran is dissolved in saline and the glucose concentration of the sample is measured by the sulfuric acid method (Dubios, 1956) using lyophilized dextran as a standard. The allyl density is calculated by subtracting the amount of glucose in the sample from the total weight of the sample. The result is assumed to be the amount of allyl hydrocarbon in the sample. The allyl concentration is then divided by the glucose concentration followed by multiplication by the average number of glucose units per dextran.

In the second step, the allyl-groups were reacted with 7.5 grams aminoethanethiol (cysteamine) in DMSO (30) to produce the amino-terminated leashes. This reaction is initiated with ammonium persulfate (99.99%, 1.0 g) and carried out at under a nitrogen atmosphere. After 3 hours the reaction volume is doubled with deionized water and the solution is adjusted to pH 4 with sodium hydroxide (2.5 N). After addition of 140 ml sodium acetate buffer (0.02 M, pH 4), the product is filtered (5 mm) into an ultrafiltration cell and dialyzed with five exchange volumes of acetate buffer (0.02 M, pH 4) followed by five exchange volumes of deionized water. After concentration, the amino-terminateddextran is then lyophilized. A sample is then assayed for the average number of amino groups per dextran, which is defined as the amino density. This lyophilized product is stored at −80° C. The mean molecular diameter is measured by laser light scattering.

Using these methods, substitution levels of 516 amino groups per molecule were determined for a amino-dextran T70, which contains an average of 388 glucose residues linked by α-1,6 and 1,4 glucosidic bonds. The mean diameter of this preparation of amino-dextran-T70 in 0.9% saline was 10.8 nanometers; the mean diameter of dextran T70 in saline was 10.6 nanometers. Using T500, which contains an average of 2881 glucose units, an average of 2900 amino leashes were found substituted.

The average number of amino groups per dextran is calculated in the following manner. The lyophilized dextran conjugate is dissolved in saline and the amine concentration is measured by the TNBS assay (Fields, 1972) using hexylamine as a standard. The glucose concentration of the same sample is also measured by the sulfuric acid method (Dubios, 1956). The amino density is calculated by dividing the amine concentration by the glucose concentration followed by multiplication by the average number of glucose units per dextran. Following are examples of how amino-dextran as formulated above can be conjugated with other compounds to synthesize various diagnostic agents.

EXAMPLE 2

Figure 2:
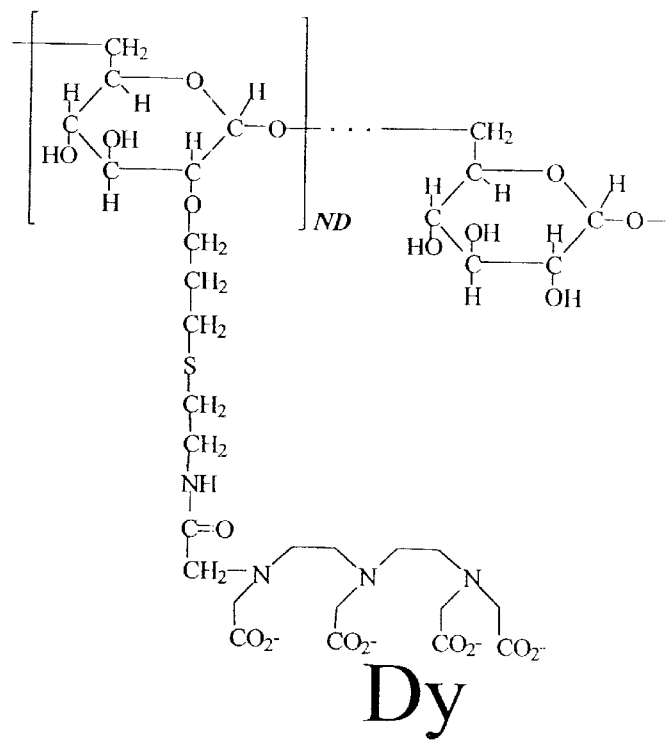
FIG. 2 shows an embodiment of the invention which is a blood pool CT agent comprising a backbone (dextran), a chelator (DPTA), and a paramagnetic atom (dysprosium).

Attachment of a Chelator (DTPA) for Blood Pool Imaging via Magnetic Resonance or Computed Tomography Attachment of diethylenetriamine pentaacetic acid (DTPA) to amino-dextran yields DTPA-amino-dextran which can in turn be labeled with gadolinium or dysprosium (see FIG. 2A) to produce a blood pool contrast agent for magnetic resonance imaging or computed tomography. The mixed anhydride method of Krejcarek et al. (1977), *Biochem. Biophys. Res. Commun.* 77:581–583, is employed. This is in addition to the novel chemistry used to first establish the leashes. This process will not promote cross-linking of the dextran if an excess of DTPA (compared to activating reagent, IBCF) is employed.

Figure 3:
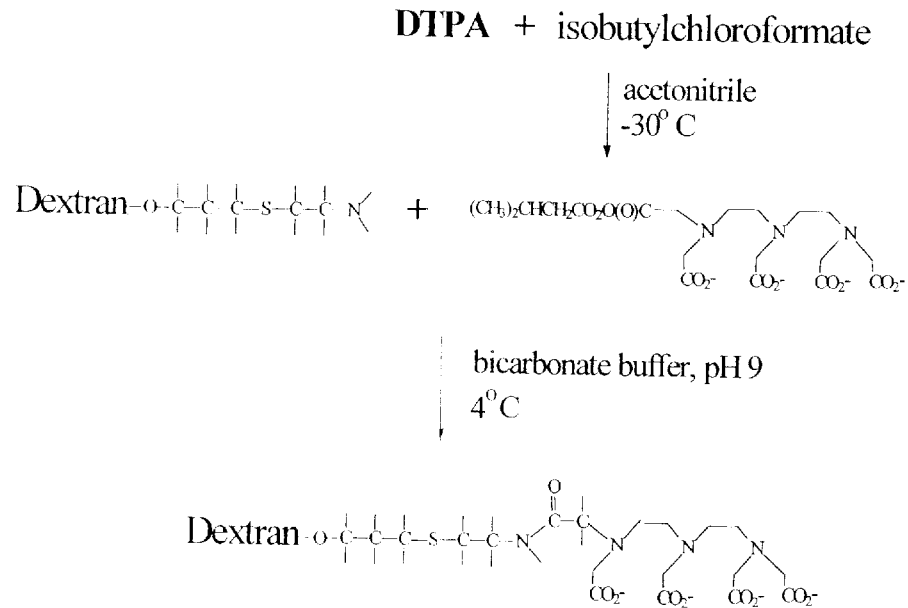
FIG. 3 shows an embodiment of a sequence for coupling of DTPA to attachment sites.

The mixed anhydride method (Krejcarek, 1977) was used to conjugate DTPA to the dextran backbone. The synthesis starts with the activation of DTPA (diethylenetriamine pentaacetic acid) (20 g) with isobutylchloroformate (IBCF) (3.1 ml). This is carried out in acetonitrile (83 ml) at −30° C. The activated DTPA is slowly added to the amino-terminated dextran (2 g) in bicarbonate buffer (0.1 M, pH 9) at 4° C. (See FIG. 3.) This solution is stirred overnight at room temperature. After extensive diafiltration the product with five exchange volumes of bicarbonate buffer (0.1 M, pH 9), followed by five exchange volumes of deionized water, the retentate is concentrated, and freeze dried. A sample is then assayed for DTPA and amino densities. This lyophilized product is stored at −80° C. The mean molecular diameter is measured by laser light scattering.

The average number of DTPA units per dextran is calculated in the following manner. Lyophilized DTPA-dextran is dissolved in 0.1 mmol/L triethanolamine HCl (pH=6.0). We added a 1.5 (mol/mol with respect to DTPA) excess of gadolinium in a 66 mM solution (filtered, 0.2 micron) of 0.1 N HCl and then adjusted the pH to 6 with 2.5 N NaOH. After stirring 24 hours at 37° C. the solution is transferred to an AMICON ultrafiltration system for diafiltration at a molecular weight cutoff of 3,000 Da. After 10 exchange volumes with deionized water followed by another 10 exchange volumes with acetate buffer (0.2 M, pH 4), the retentate is concentrated and assayed for gadolinium concentration by ICP spectrometry (Vera, 1995). The glucose concentration of the same sample is also measured by the sulfuric acid method (Dubios, 1956). The DTPA density is calculated by dividing the gadolinium concentration by the glucose concentration followed by multiplication by the average number of glucose units per dextran.

Figure 4:
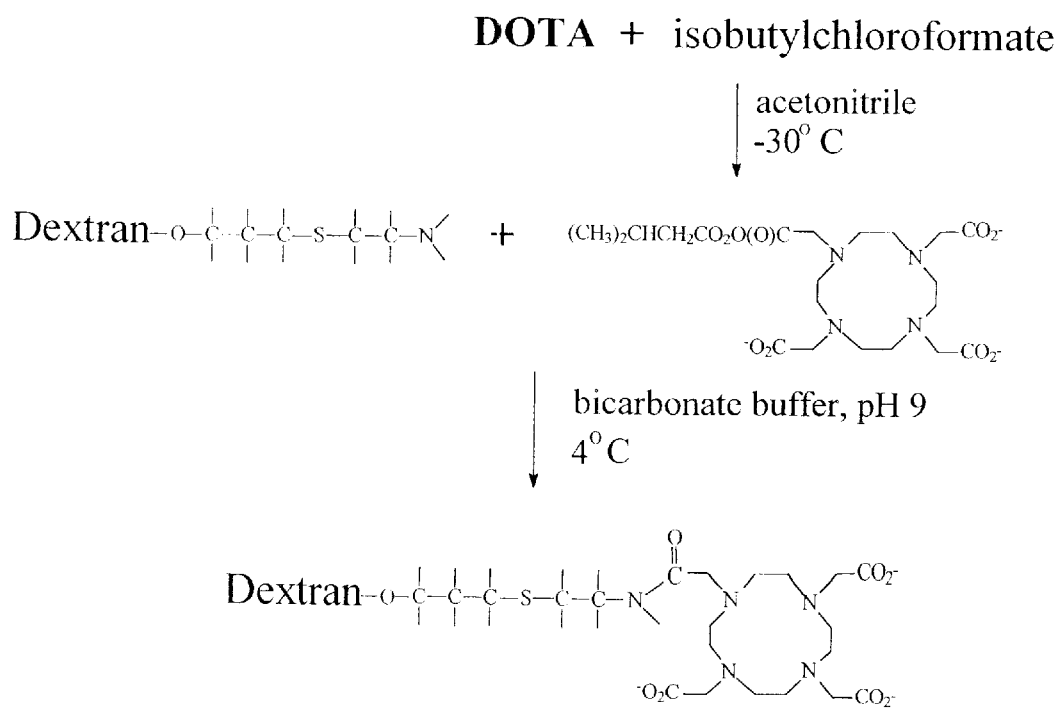
FIG. 4 shows an embodiment of a sequence for coupling of DOTA to attachment sites.
Figure 5:
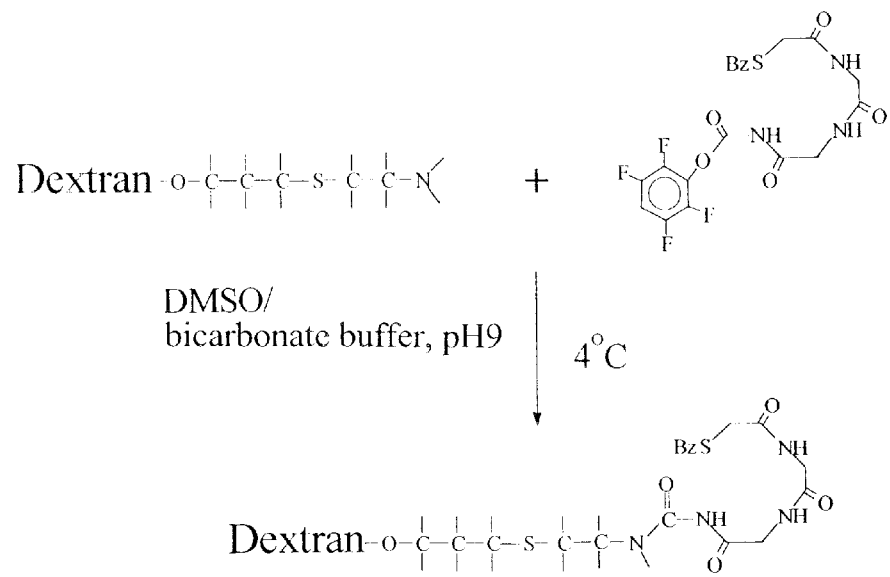
FIG. 5 shows an embodiment of a sequence for coupling of MAG3 to attachment sites.

Procedures for coupling of other chelators, including DOTA and MAG3, to attachment sites are shown in FIGS. 4 and 5, respectively.

EXAMPLE 3

Attachment of Mannose for Lymph Node and Liver Imaging

The presence of mannose appended to the dextran backbone will target the compound, depending on the mode of administration, to a receptor (mannose binding protein) that resides on liver, spleen, lung, bone marrow and lymph nodes. Steer C J, Ashwell G (1990). Receptor-mediated endocytosis: Mechanisms, biologic function, and molecular properties. In: Hepatology. A Textbook of liver Disease. (2nd Ed.) Zakim D, Boyer T D, eds. W. B. Saunders, Philadelphia. If the compound is administered subcutaneously, the mannose-terminated dextran will enter the lymphatic system and bind to receptors within lymph nodes; if administered intravenously, binding will occur to the liver, spleen, lung and bone marrow. It is further known that mannose-binding protein exhibits increased affinity to cluster glycosides, e.g., mannose and mannose-derivatized compounds.

Figure 6:
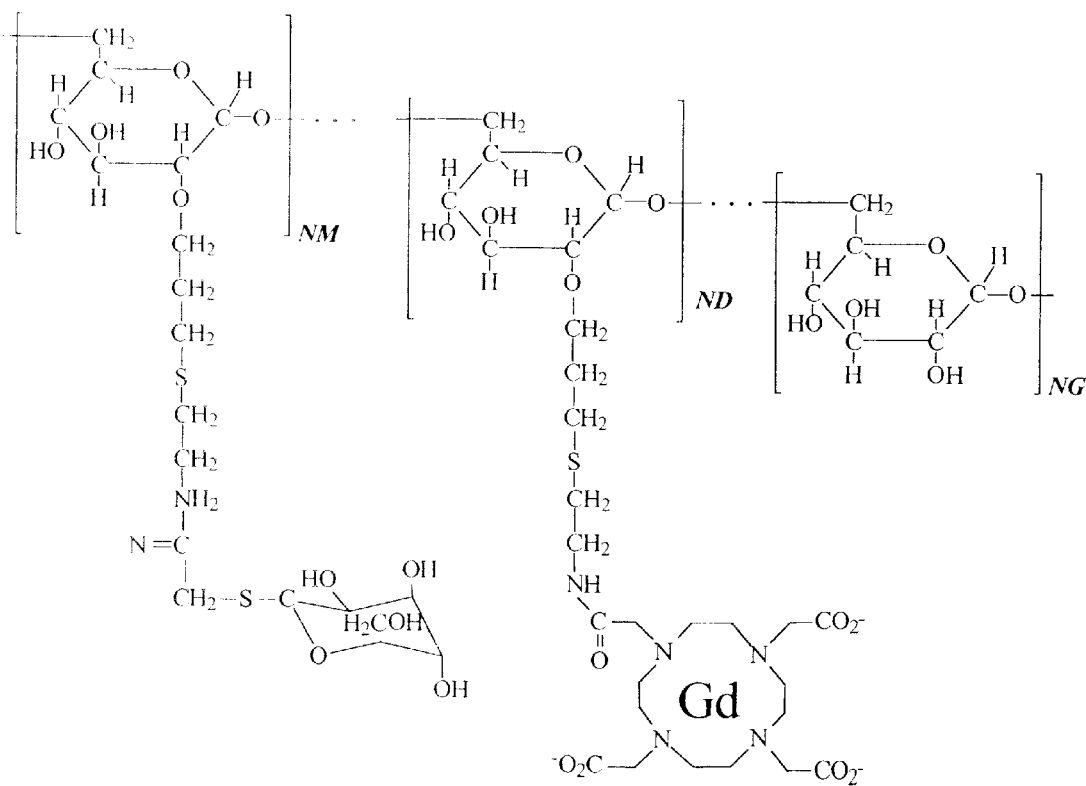
FIG. 6 shows a lymph node MRI Agent embodiment comprising a receptor substrate (mannose), a backbone (dextran), a chelator (DOTA), and a MRI reporter (gadolinium).
Figure 7:
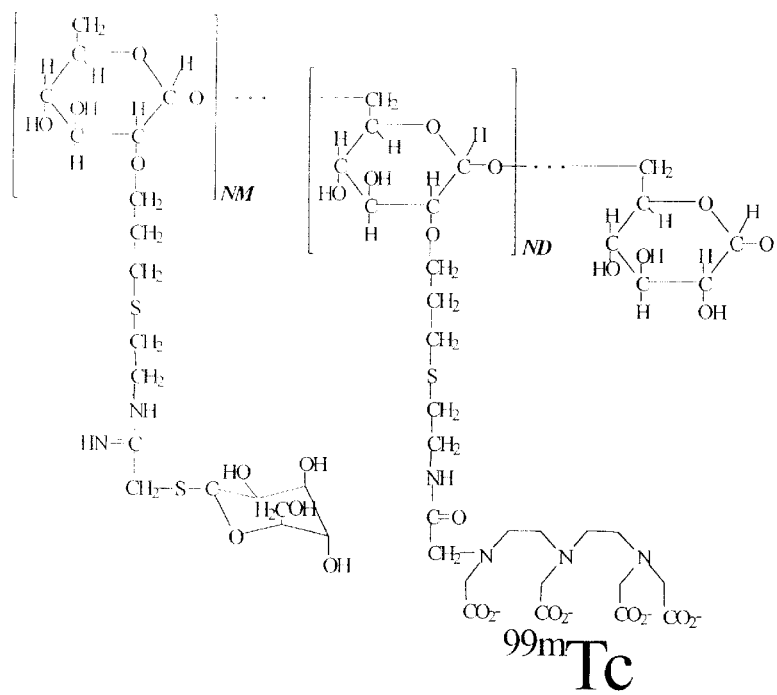
FIG. 7 shows the formula for an embodiment of a sentinel node detection agent comprising a receptor substrate (mannose), a backbone (dextran), a chelator (DTPA), and a radioactive atom (Tc-99).

If the dextran backbone is also made to carry a chelating agent such as DTPA or DOTA (Sieving et al. (1990), *Bioconj. Chem.* 1:65–71), the resulting combination can further be labeled with gadolinium, technetium-99m, or ytterbium. Gadolinium (see, e.g., FIG. 6) permits the detection of liver or lymph node tumors via magnetic resonance imaging. The radiolabel technetium-99m (see, e.g., FIG. 7) permits liver or lymph node imaging by scintigraphy. Ytterbium, like gadolinium and dysprosium, permits imaging via computed tomography.

The chemical attachment of mannose to amino-dextran can be accomplished by a number of methods, e.g., that described for attachment to human serum albumin (Vera et al. (1985) *J. Nucl. Med.* 26:1157–1167) and that described for attachment to polylysine (Vera et al.(1995) *Acad. Radiol.* 2:497–596). See, e.g., FIG. 8. This attachment can be carried out as described above for galactose.

Figure 8:
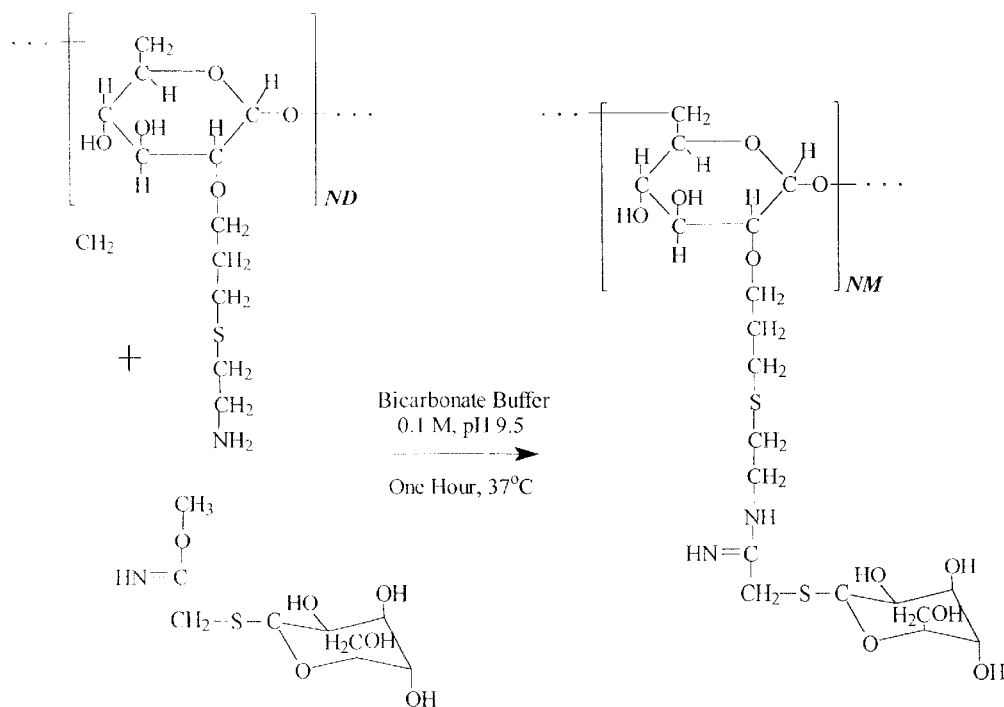
FIG. 8 shows an embodiment of a procedure for coupling of mannose to the attachment sites.

Conjugation of DTPA-dextran with mannose is accomplished by reductive alkylation (Vera, 1997). The mannosyl coupling reagent, cyanomethyl 2,3,4,6-tetra-O-acetyl-1-thio-β-D-mannoside (CNM-thiomannose), is synthesized by the following route. Tetra-O-acetyl-α-D-mannopyranosyl bromide (this carbohydrate is not commercially available) is produced by a two-step reaction in chloroform (Lee, 1994). After rotary evaporation to a syrup, the product is immediately reacted with thiourea to produce 2-S-(2,3,4,6-tetra-O-acetyl-β-D-mannopyranosyl)-2-peusdothiourea-hydrobromide (Chipowsky, 1973), which is recrystallized in acetone. Immediately prior to mannosyl conjugation, this product is deacetylated with sodium methoxide (0.05 mg/ml) in dry freshly distilled methanol (250 ml) using a CNM-thiomannose concentration of 0.04 gram per ml of methanol. After removal of the methanol by rotary evaporation, the coupling reaction is carried out by the addition of an appropriate amount of DTPA-dextran (0.5 gram) in a 20 mg/ml solution of bicarbonate buffer (0.2 M, pH 9.0). The reaction is conducted at room temperature 2 hours (FIG. 8). After diafiltration the product with five exchange volumes of bicarbonate buffer (0.1 M, pH 9), followed by another five exchange volumes of deionized water, the retentate is concentrated, and freeze dried. A sample is then assayed for mannose, DTPA, and amine densities. This lyophilized product is stored at −80° C. The mean molecular diameter as measured by laser light scattering is 7.6 nm.

The average number of mannose groups per dextran is calculated in the following manner. The lyophilized dextran conjugate is dissolved in triethanolamine and labeled with gadolinium as described above. After diafiltration and measurement of DTPA concentration, the mannose concentration of the same sample is also measured by the sulfuric acid method (Dubios, 1956). The mannose density is calculated by dividing the mannose concentration by the dextran concentration, which is calculated based on the known DTPA density of the DTPA-dextran conjugate.

A sentinel node imaging agent DTPA-mannosyl-dextran was synthesized using pharmaceutical grade dextran, PM10. See, e.g., FIG. 7. This preparation had a mean diameter of 7.6 nanometers, mannose density of 44 units per dextran, an amine density of 23 units per dextran, and a DTPA density of 8 units per dextran. The molecular weight was 36,288 grams per mole.

EXAMPLE 4

Attachment of Galactose for Liver Imaging

The presence of the substrate galactose can deliver the dextran to a receptor that resides exclusively in the liver. If the dextran is also carrying DTPA, it can be labeled with gadolinium or technetium-99m. The use of gadolinium permits the detection of liver cancer via magnetic resonance imaging. The radioactive label technetium-99m permits liver imaging by scintigraphy.

Figure 13A:
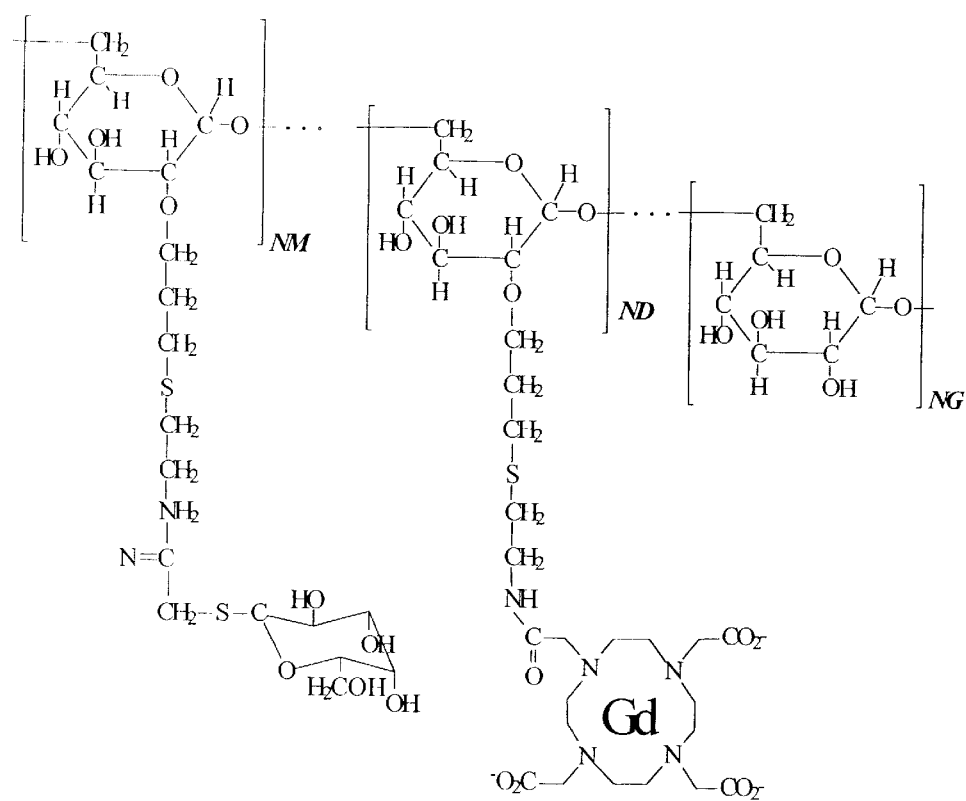
FIG. 13a shows the formula for an embodiment of a hepatocyte-targeted MR imaging agent comprising a receptor substrate (galactose), a backbone (dextran), a chelator (DOTA), and a paramagnetic atom (Gd).
Figure 13B:
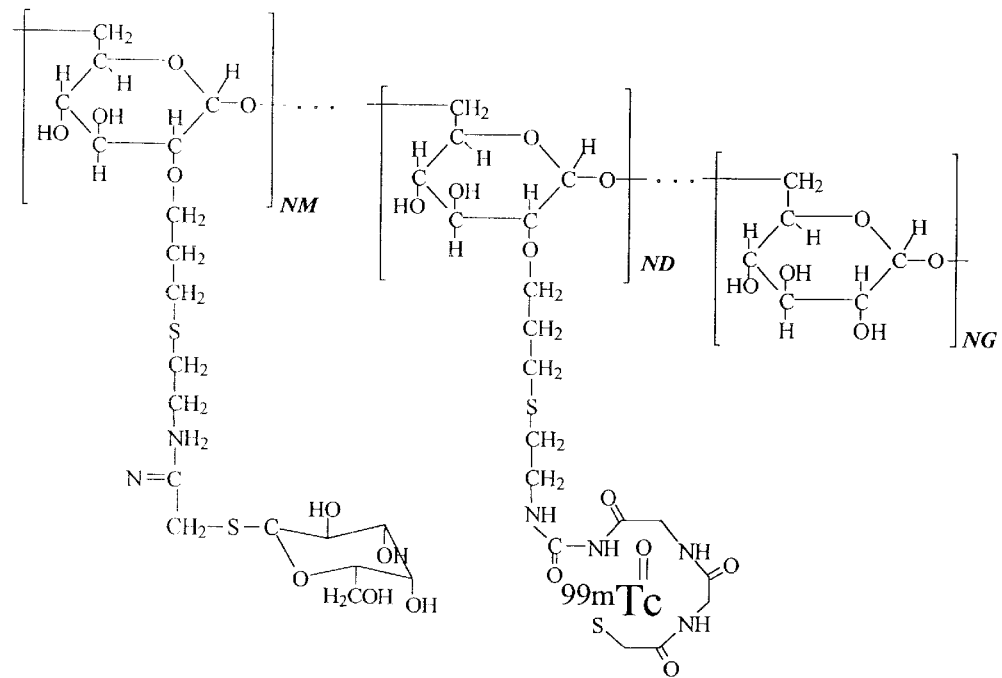
FIG. 13b shows the formula for an embodiment of a hepatocyte-targeted nuclear imaging agent comprising a receptor substrate (galactose), a backbone (dextran), a chelator (MAG3), and a radioactive atom (Tc-99m).

The chemical attachment of galactose to amino-dextran can be accomplished by a number of methods, e.g., as described for attachment to human serum albumin (Vera et al. (1985) *J. Nucl. Med.* 26:1157–1167) and polylysine (Vera et al.(1995) *Acad. Radiol.* 2:497–596). The coupling reaction for the attachment of galactose to amino-terminated dextran is the same as the attachment (see below) of mannose. FIGS. 13A and 13B are examples of an MR liver imaging agent and a nuclear medicine imaging agent, both of which use an embodiment of the invention.

EXAMPLE 5

Attachment of MAG3 Chelator for Nuclear Imaging

Conjugation of amino-terminated dextran starts with the activation of mercaptoacetylglycylglycyl-glycine (MAG3) (Fritzberg, 1986) with tetraflorophenol (TFP). This is carried out with an equivalent amount of 1,3 dicyclohexylcarbodiimide (DCC) in N,N-dimethylformamide (DMF) at room temperature. This solution is rotary evaporated, dissolved in chloroform, and filtered. This resulting solution is rotary evaporated and the solution product, TFP-MAG3 stored in the freezer. Finally, the aminoterminated-dextran in a DMSO/water solution (1:10) is combined with TFP-MAG3 in a similar solution. This solution is stirred overnight at room temperature. After extensive diafiltration with water the product is concentrated and freeze dried.

Sentinel Node Imaging: Prospects for The Improved Diagnosis and Treatment of Cancers, i.e., Breast Cancer, Melanoma, and Colorectal Cancer In a effort to reduce the morbidity and costs of detection for lymph node metastases, surgical oncologists have developed a method by which the sentinel lymph node (the first node in a draining basin) is identified intraoperatively and removed (Morton et al. (1992) *Arch. Surg.* 127:292–299.). This technique, called sentinel node biopsy, has extremely high negative predictive values for melanoma and breast cancer metastases (Giuliano et al. (1994) *Arch. Surg.* 220:391–401); the false-negative rates range from zero to 9% for both cancers. There is also growing evidence that sentinel node biopsy will have a significant impact on the management of colorectal cancer (Saha et al. (1998) *J. Surg. Oncol.* 69:183.).

As stated, sentinel node imaging is a nuclear medicine examination which identifies for the surgeon the first lymph node to receive lymphatic flow from the primary tumor site. This node is removed and sent for frozen section analysis for detection of malignant cells. By identifying the sentinel node prior to surgery, a small incision can be use to remove the node and a smaller dissection can be employed. The extremely high negative predictive value of the technique seems to provide an accurate staging procedure and may spare patients who are sentinel node negative the morbidity of a complete lymph node dissection. Consequently, staging of the cancer by sentinel node imaging may be equivalent to axillary node dissection without the attendant post-surgical morbidity.

When performing sentinel node biopsy, the imaging agent is injected around the tumor site and a hand held gamma probe is used to find and remove the sentinel node. Often, however, the nuclear activity either spills over into the nodal basin making differentiation between node and tumor difficult, or it disseminates into multiple nodes causing more than the necessary number of nodes to be removed.

An ideal sentinel node imaging agent would exhibit rapid clearance from the injection site, high retention within the lymph channel, rapid, complete, and sustained uptake by the sentinel lymph node, and low uptake by the remaining lymph nodes. In breast cancer cases the sentinel node is sometimes not found because the tumor site is so close to the sentinel node, with radioactivity between the two sites being indiscernible. The standard features of low radiation absorption, high biological safety, convenient, rapid, and stable technetium-99m labeling, and biochemical purity also apply.

Filtered colloids exhibit poor clearance from the injection site. The half times for filtered Tc-albumin colloid and Tc-sulfur colloid are 5.5 hr and 10.5 hr, respectively (Glass, 1995). This translates to approximately 65% and 85% of the dose at the injection site at 3 hours postinjection, the optimal time for the intraoperative search for the sentinel node (Uren, 1995). Conversely the labeled macromolecules, such as Tc-dextran and TC-HSA ($T_{1/2}$=2.8 hr), offer the fastest clearance (Henze, 1982; Glass, 1995).

Figure 9:
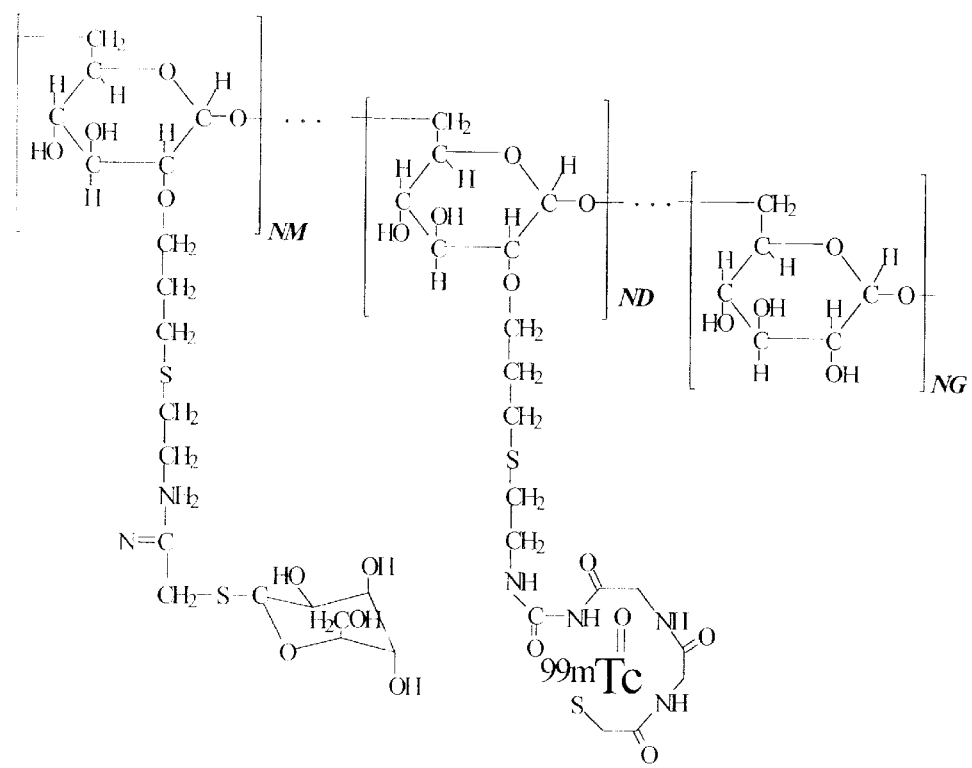
FIG. 9 shows the formula for an embodiment of a sentinel node detection agent comprising a receptor substrate (mannose), a backbone (dextran), a chelator (MAG3), and a radioactive atom (Tc-99m).

The procedures described for the present invention improve the combination of technetium-99m-labeled MAG3-mannosyl-dextran. This agent has already been demonstrated effective, even when prepared using the suboptimal, cross-link-prone procedures of the prior art. Technetium-99m-labeled MAG3-mannosyl-dextran, as previously described, is a 10-kilodalton molecule of dextran to which multiple units of mannose and MAG3 are attached. This molecule has a mean diameter of 5.5 nanometers (nm), which is substantially smaller than Tc-99m antimony trisulfide (10 nm), filtered Tc-99m sulfur colloid (50 nm), and unfiltered Tc-99m sulfur colloid (650 nm), which had previously been the prevailing standards. The employment of mannose acts as a substrate for the mannose-binding protein receptor and the MAG3 serves as a chelating agent for labeling with technetium-99m (FIG. 9). The resulting radiolabeled conjugate rapidly clears the injection site and binds to the sentinel lymph node. That prior study is reproduced below; use of the improved chemistry described herein promises to only enhance the success already obtained.

EXAMPLE 6

Demonstration of Sentinel Node Imaging In Rabbits

Figure 10:
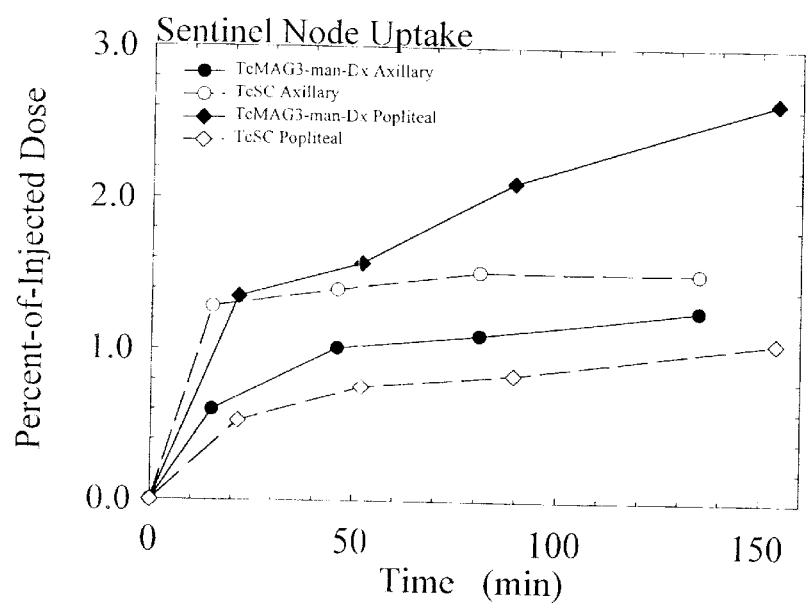
FIG. 10 is a plot of percent of injected dose versus time showing sentinel node uptake of TcMAG3-mannosyl-Dextran (closed symbols) and Tc-sulfur colloid (closed symbols).
Figure 11:
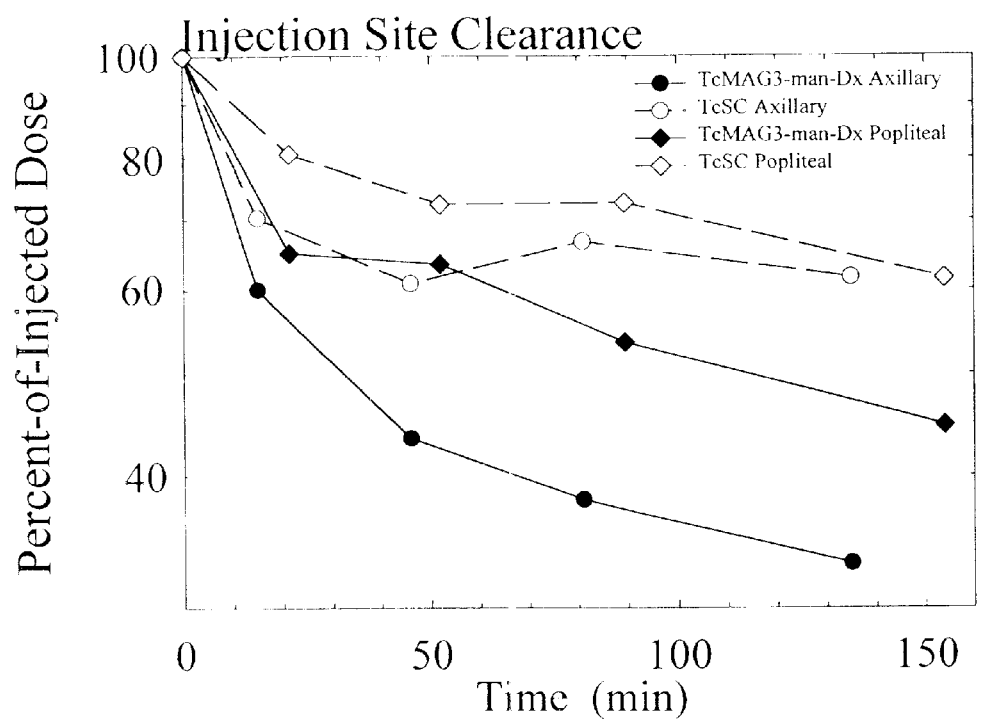
FIG. 11 is a plot of percent of log injected dose versus time showing injection site clearance of TcMAG3-mannosyl-Dextran (closed symbols) and Tc-sulfur colloid (open symbols).

After anesthesia with an intramuscular injection of ketamine and xylazine, 0.5 ml of TcMAG3-mannosyl-dextran (19,000 g/mole) was injected to the right front (0.42 mCi) and right rear (0.43 mCi) foot pads and 0.5 ml of filtered Tc-sulfur colloid to the left front (0.41 mCi) and left rear (0.42 mCi) foot pads. The rabbit was hydrated with 10 cc of saline infused to the neck every 60 minutes. After injection of each radiopharmaceutical, the foot pads were massaged for 5 minutes. Periodic static images (1,000 kcts, 256×256× 16) were acquired on a large field-of-view gamma camera (high resolution, low energy collimator) at 15, 45, 100, and 135 minutes with the front limbs and axillary nodes in view, and at 21, 53, 109, and 154 minutes with the rear limbs and popliteal limbs in view. The limbs were exercised for 15 minutes before each image. Imaging standards (10×dilution) of both TcMAG3-mannosyl-dextran and the TcSC were also positioned within the field-of-view. Approximately 150 minutes post-injection the rabbit was euthanized. Each sentinel node was excised and assayed for radioactivity with diluted (2-fold) samples of the TcMAG3-mannosyl-dextran and TCSC doses. These values were normalized by each imaging standard to yield the sentinel node %ID, which were then plotted as a function of time (FIG. 10). For each serial image, regions-of-interest (ROIs) were drawn around the injection site, sentinel node, and imaging standards. The total counts within each ROI were then calculated using standard nuclear medicine software. The absolute counts in the injection site ROI's were then divided by the counts of the standard and the fraction-of-injected dose was calculated. These values were then plotted on a logarithmic scale, shown in FIG. 11.

The data obtained demonstrates that the imaging properties of Tc99m-MAG3-mannosyl-dextran are superior to the filtered Tc99m sulfur colloid. The percent-of injected dose, plotted in FIG. 10, demonstrated greater lymph node uptake of TcMAG3-mannosyl-dextran in both axillary and popliteal sentinel nodes over a 150-minute period. Additionally, TcMAG3-mannosyl-dextran exhibited significantly faster clearance from the injection site, indicated by the lower curve of FIG. 11.

Figure 12:
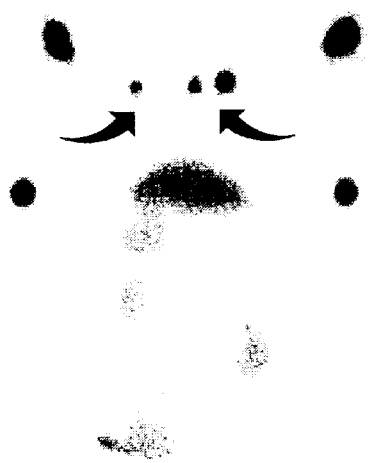
FIG. 12 shows rabbit axillary lymph nodes (indicated by arrows) imaged 15 minutes after subcutaneous administration of TcMAG3-mannosyl-dextran (right footpad) and TcSC (left footpad). The injection sits are at the top of the image. There are a pair of standards at either side of the rabbit. In addition to the bilateral sentinel nodes, a focus of activity adjacent to the left sentinel node medially may represent TsSC activity in a distal node.

Axillary lymph nodes imaged 15 minutes after administration of TcMAG3-mannosyl-dextran and TcSC appeared as shown in FIG. 12. The injection sites are at the top of the image (TcMAG3-mannosyl-dextran on the left and TcSC filtered on the right side). There is a pair of standards at either side of the rabbit. In addition to the bilateral sentinel nodes, a focus of activity adjacent to the left sentinel node medially may represent TcSC activity in a distal node, corresponding to the frequently observed behavior of TcSC where distal lymph nodes are commonly observed in delayed images. This activity, however, may represent a mediastinal lymph node shared by both sides of the axillary lymphatic chain, in which case this finding will not be of much significance.

The rapid injection site clearance of TcMAG3-mannosyl-dextran may be explained by the small size of the particle (5.5 nanometers), which allows it to also diffuse into the blood capillaries.

Lymph node uptake of TcMAG3-mannosyl-dextran for the three rabbit studies ranged from 1.2 to 2.5 percent of the injected dose. The range for filtered TcSulfur Colloid was 1.5–4.9 percent.

EXAMPLE 7

Demonstration of Blood Pool Magnetic Resonance Imaging In Rabbits

Figure 19A:
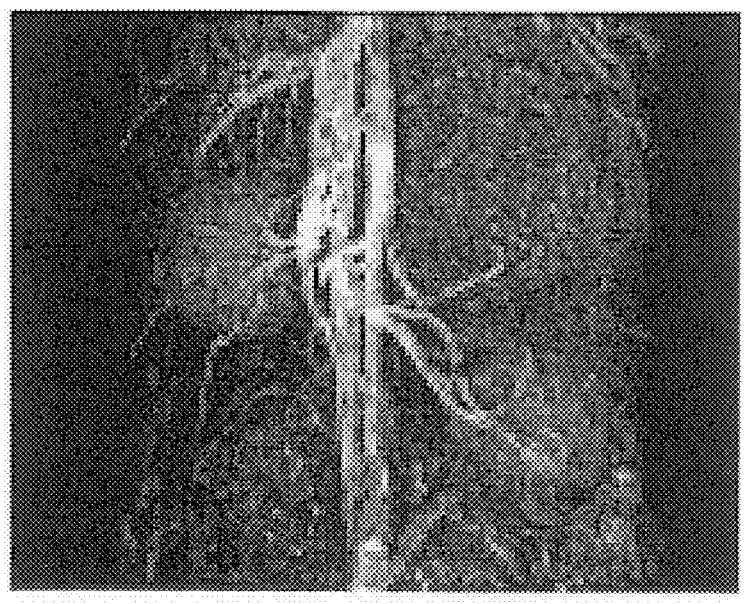
FIGS. 19a–b are examples of MR blood pool imaging using and embodiment of the invention where
Figure 19B:

Magnetic resonance imaging with GdDTPA-dextran was performed using both one healthy and one tumor-bearing rabbit weighing 3.0 and 2.7 kg, respectively. Each rabbit was anesthetized with a mixture of 50 mg/kg Ketamine and 8.8 mg/kg Xylazine. Following anesthesia administration each rabbit was then intubated with a 3-mm tracheal tube and positioned within the scan field. Each rabbit was ventilated at 60 bpm with a stroke volume of 25 cc, which permitted respiratory gating. Both rabbits received a 0.17 mmole gadolinium-per-kilogram dose (0.13 grams GdDTPA-Dx/ kg) of GdDTPA-dextran (MW=398,000 g/mole, 515 Gd per dextran). Images were acquired using a GE Signa™ 1.5 T magnetic resonance imaging unit (Version 4.83 software) (GE Medical Systems, Milwaukee, Wis.) with each rabbit placed in a knee coil. We explored a number of acquisition parameters; the most successful was a 3D time of flight (TOF) fast spoiled gradient echo (FSPGR) sequence: TR=15.1 msec, TE=4.2 msec, flip angle=30°, 256×192 matrix, 16 cm FOV, 80 slices of 1.5 mm thickness. Images of the healthy rabbit (3 kg) were acquired prior to injection (2.0 ml), and at 15, 28, 33, 46 minutes, and 3 hours post injection. With the exception of the 28-minute scan, which was in the coronal plane, all scans were acquired in the axial projection. The uncorrected signal intensities within the aorta at the level of the right kidney were: pre-injection, 193; 28 minutes, 552; 33 minutes, 516; and 46 minutes, 472. FIG. 19a is a maximum intensity projection image of the healthy rabbit acquired 15 minutes post-injection. FIG. 19b is a similar image of the same animal acquired three hours post-injection.

FIGS. 16a and 16b are magnetic resonance images of the tumor-bearing rabbit (2.7 kg). The tumor is a VX2 carcinoma in the right hind leg. The tumor vessels are not visible in FIG. 16a, which was acquired before the GdDTPA-dextran injection (1.8 ml, 0.17 mmole Gd/kg). One hour after administration of GdDTPA-dextran the tumor vessels are easily visualized (FIG. 16b). Based on axial 3D FSPGR images (TR=15.1 msec, TE=4.2 msec) we calculated the contrast-to-noise ratio CNR by measuring the mean signal intensity within the tumor region-of-interest (ROI), subtracting the mean signal intensity from muscle, and dividing the result by the standard deviation of an ROI taken from a region outside the body. The CNR for a region within the center of the tumor was 0.63 before injection and 9.6 fifty-four minutes after GdDTPA-dextran administration. The CNR for blood vessel within the tumor was −21.4 before injection and 120 after administration. The negative number is the result of a higher signal for muscle than the unenhanced tumor vessel.

Our 54-minute CNR of 120 is approximately three-fold higher then the typical values (CNR=42) reported (Grist TM et al. *Radiology* 207:539–544.) in the human aorta using MS-325, the albumin-targeted agent at a similar time post-injection.

EXAMPLE 8

Demonstration of Blood Pool Computed Tomography In Rabbits

Two rabbits were scanned on a G.E. 9800 Quick™ CT scanner. One rabbit (2.6 kg) bearing a large VX2 tumor was imaged with DyDTPA-T40 (MW=101,537 g/mole, 95 Dy per T40) and a second healthy rabbit (3 kg) was imaged with Optiray-320 (MW=807 g/mole). Each rabbit was anesthetized with a mixture of 50 mg/kg Ketamine and 8.8 mg/kg Xylazine. Following anesthesia administration each rabbit was intubated with a 3-mm tracheal tube and positioned within the scan field. Each rabbit was ventilated at 60 bpm with a stroke volume of 25 cc to allow for breath holding during each image. A localization image was then obtained to discern the location of the heart, tumor, right lobe of the liver, kidney and spleen. All subsequent images were obtained using 120 KV, 200 mA, 3 mm slice thickness, 2 sec scan time, 512 matrix, and FOV of 16 cm. Serial images, 3 mm apart, were taken from the middle of the heart to the middle of the left kidney. From this image series, axial positions were selected for the heart, liver, tumor, kidney and spleen. After three images at each position we injected [Dy]DTPA-T40 (5 ml, 190 mg Dy/kg, 37 mmole Dy/kg) over a 120-second period and acquired images at 2, 5, 7, 15, 30 and 37 minutes post-injection. Images for the tumor-bearing rabbit taken before injection and at 2, 5, 30 and 37 minutes post-injection are shown in FIGS. 17a–e, respectively. We injected the Optiray-320 (640 mg l/kg, 5.0 mmole l/kg) over a 60-sec period and imaged at 2 through 10 minutes at one-minute intervals and at 20 minutes after injection.

Figure 14A:
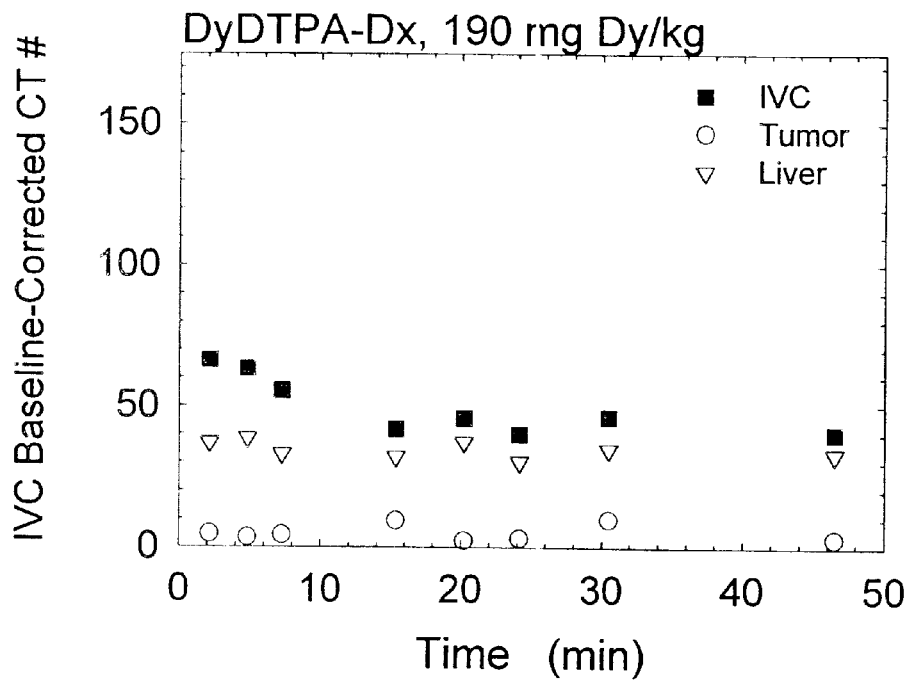
FIG. 14a shows the enhancement time course in the inferior vena cava, liver, and tumor after an injection of a CT blood pool imaging agent using an embodiment of the invention DyDTPA-dextran.
Figure 14B:
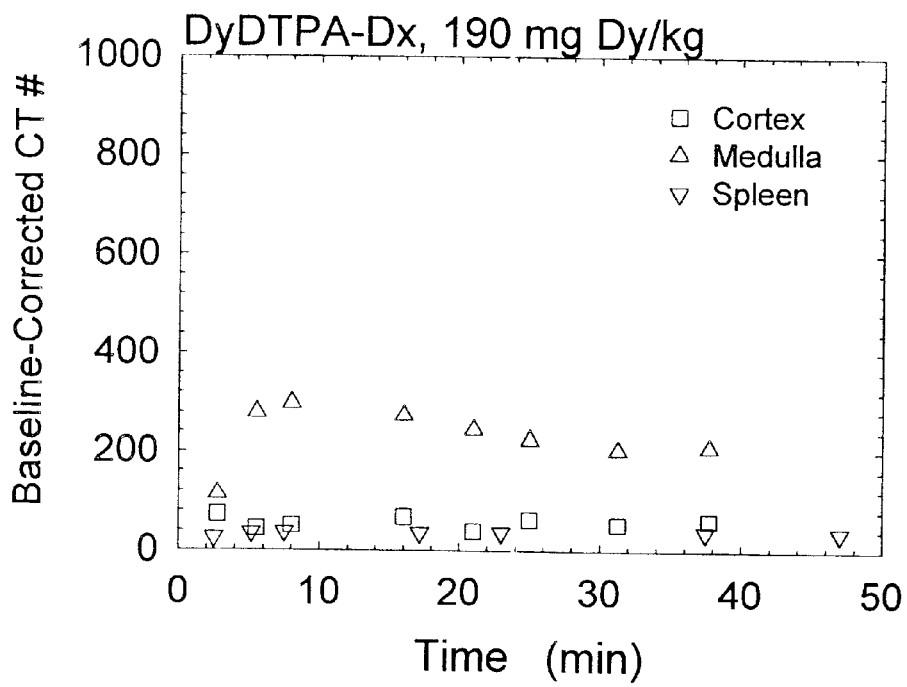
FIG. 14b shows the enhancement time course in the renal cortex, renal medulla, and spleen after an injection of a CT blood pool imaging agent using an embodiment of the invention DyDTPA-dextran.
Figure 14C:
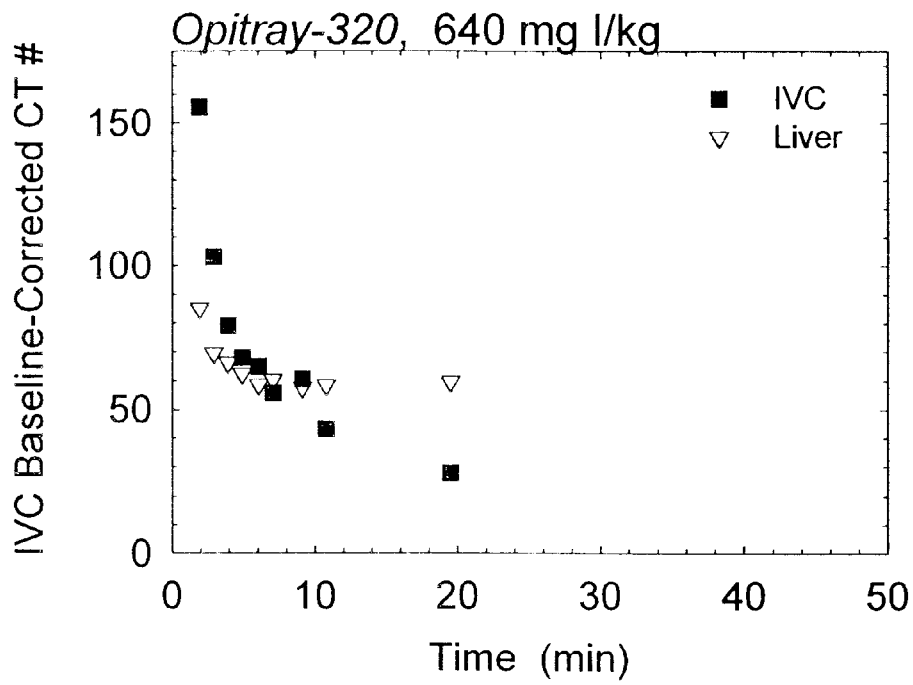
FIG. 14c shows the enhancement time course in the inferior vena cava, and liver after an injection of a commercially available CT contrast agent, Opitray-320.
Figure 14D:
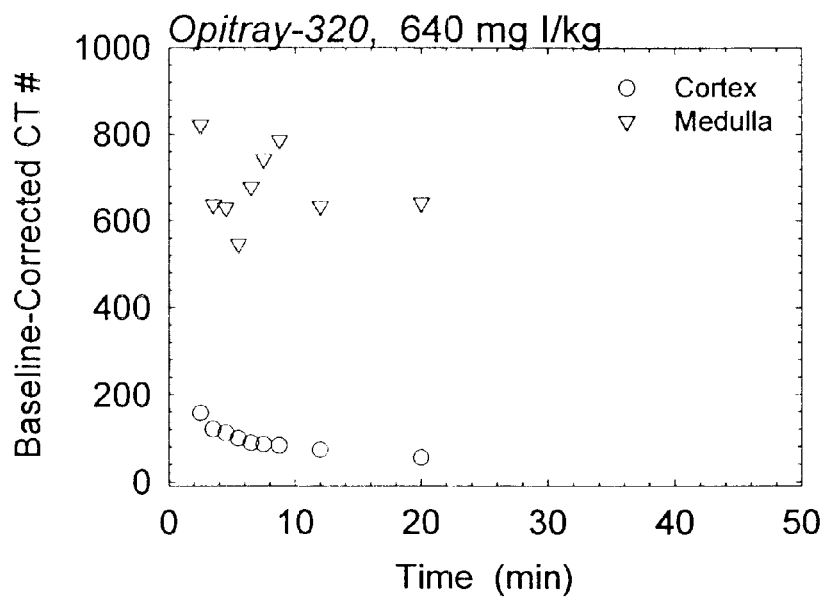
FIG. 14d shows the enhancement time course in the renal cortex, and renal medulla after an injection of a commercially available CT contrast agent, Opitray-320.
Figure 17A:
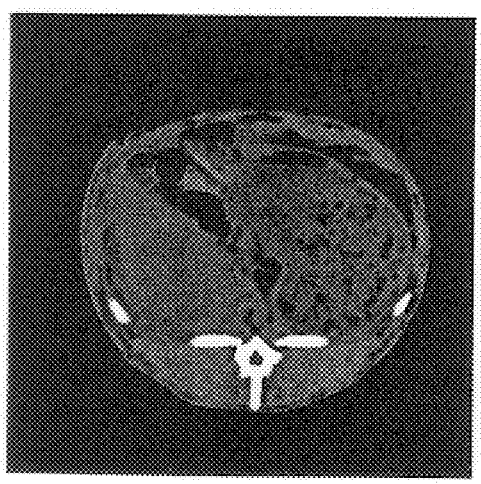
FIGS. 17a–e are examples of CT blood pool images of a tumor-bearing rabbit taken before injection and at 2, 5, 30 and 37 minutes after [Dy]DTPA-T40 injection, respectively.
Figure 17B:
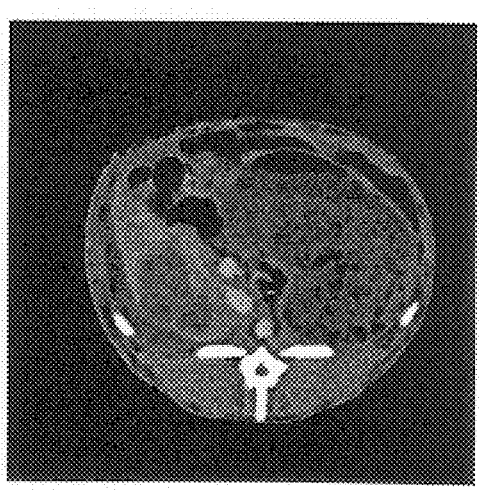
Figure 17C:
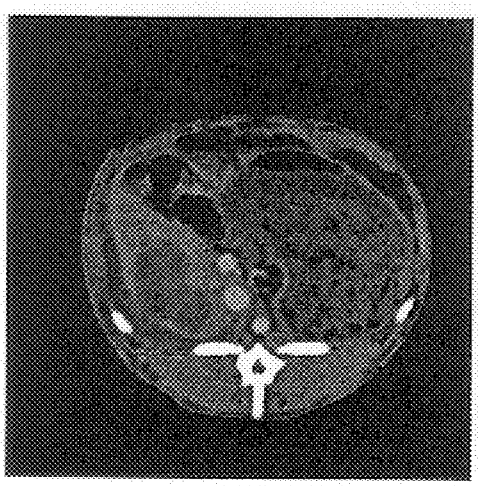
Figure 17D:
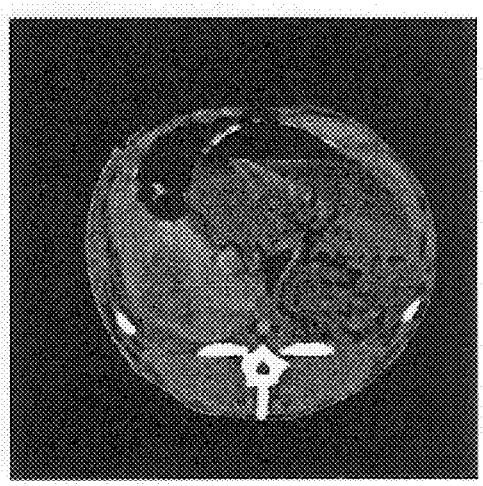
Figure 17E:
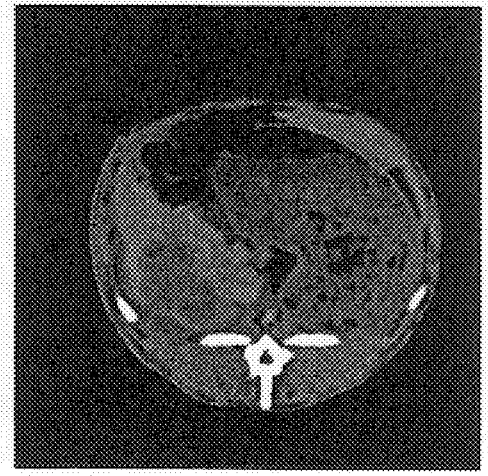
Figure 18A:
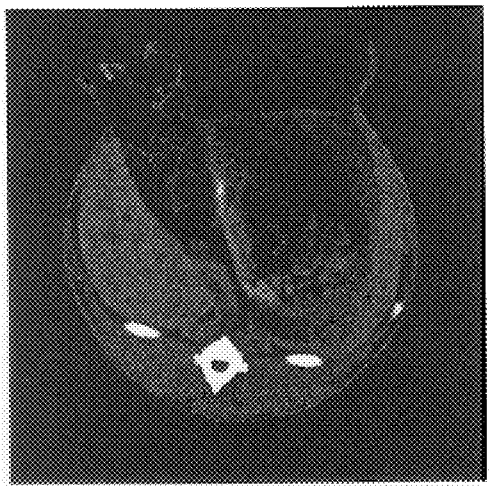
FIGS. 18a, 18b, 18c and 18d are CT blood pool images showing a time series of liver cross-sections before (FIG. 18a) and 2 minutes (FIG. 18b), 5 minutes (FIG. 18c), and 10 minutes (FIG. 18d) after an injection of Optiray-320 into a healthy rabbit.
Figure 18B:
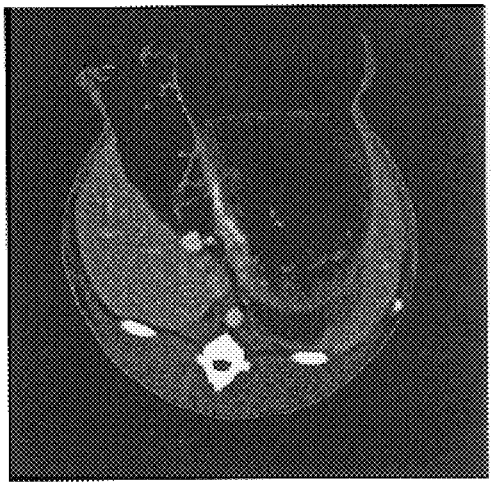
Figure 18C:
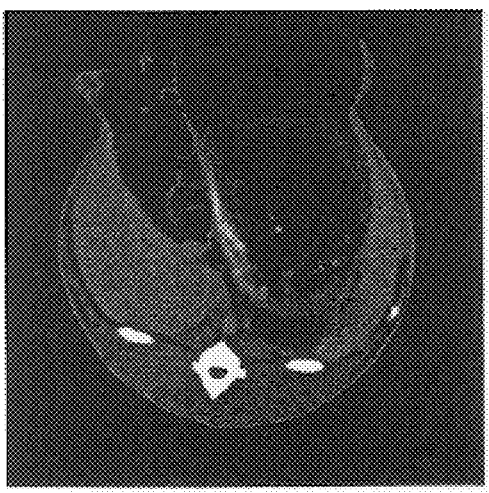
Figure 18D:
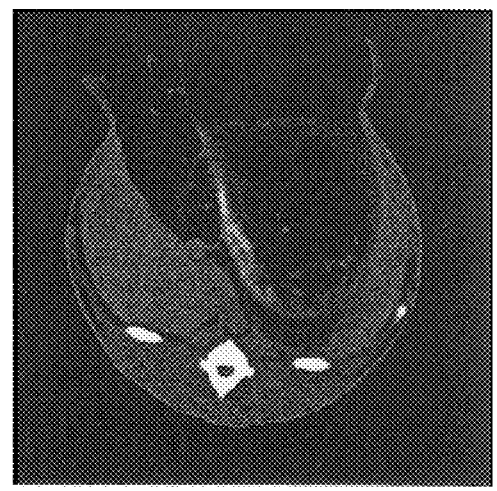

FIGS. 18a, 18b, 18c and 18d are a time series of liver cross-sections before and 2, 5, and 10 minutes after an injection of Optiray-320 into a healthy rabbit. Only the five-minute image shows the aorta, IVC and portal vein at a greater intensity than the liver. The two and five minutes images (FIGS. 18b and 18c, respectively) in the DyDTPA-T40 time series show these vessels, as well as, intra-hepatic vessels with a greater intensity then the surrounding liver. The IVC and liver baseline-corrected curves (FIGS. 14a–d) for both agents are consistent with the images. Most important, is that the IVC curve for DyDPTA-T40 persists for at least ten minutes, while the Optiray-320 IVC curve has rapidly declined with a half-time of approximately two minutes. The y-axis of the curves in FIGS. 14a–d were calculated by subtracting the CT# of the IVC ROI from the liver CT#. Our purpose was to remove the baseline and preserve the difference between vessel and liver signals. Also significant is the lack of uptake of DyDTPA-Dx by the spleen and renal cortex, as indicated in FIG. 14b. The renal medulla intensity indicates filtration of either intact macromolecule, Dy dissociated from the chelate, or and Dy-metabolic product.

To test for evidence of dextran crosslinking resulting from our leash attachment chemistry we chromatographed a amino-terminated-T10 conjugate (NT10) using Sephacryl S-300HR (27×1 cm) and 0.9% saline as the mobile phase (30 ml/hr). We monitored the elution at 226 nm. Pharmacia lists the useful fractionation range for dextran as $2 \times 10^3$–$1 \times 10^5$ Da. FIG. 15a is a chromatogram of human serum albumin; the void volume is at Vo and the total volume is at Vt. FIG. 15b is a chromatogram of the amino-terminated-T10 conjugate, which has 105 leashes; this is a leash density of 1.8 amino groups per glucose unit. Evidence of crosslinking would occur at the void volume, where the absorbance profile would immediately rise in response to the presence of high molecular weight dextran. The mean diameter of this conjugate, as measured by dynamic laser light scattering (Honeywell Microtrac™ UPA150), was 0.043 micron, with a standard deviation of 0.0010 microns. The albumin was measured at 0.0092–/+0.0011 micron, which is slightly higher than the published diameter of 0.0072 micron.

DISCUSSION

The advantages and useful contributions of the two-step leash attachment scheme described herein are: high attachment yield, low cross-linking, and the lack of charge at the attachment site. The dextran backbone further offers low-cost and extensive human-use experience. The existence of a large number of leashes (i.e., amino groups) per dextran molecule also permits the attachment of a high density of substrates and/or drugs to each dextran backbone.

Methods prior to the invention produced unwanted cross-linking of the molecular backbone. See, e.g., Rebizak et al. (1997), *Bioconj. Chem.* 8:605–610; Rebizak et al. (1998), *Bioconj. Chem.* 9:94–99 (describing reaction of ethylenediamine with dextran carboxylic acid in the presence of 2-ethoxy-1-(ethoxycarbonyl)-1,2-dihydroquinoline (EEDQ)). Cross-linking is a serious problem because it increases the molecular weight of the backbone, consequently decreasing the solubility of the product. Furthermore, it may induce toxicity by destabilizing the complexation constant between the highly toxic radiotracer (e.g., $Gd^{3+}$) and chelator group in such macromolecular structures. As a result, these conventional reaction schemes can only be used to attach a low density of leashes per molecule of dextran; accordingly, conventional procedures permit the dextran molecule to carry only a few substrates and/or drugs, thereby requiring higher doses of dextran to achieve the desired diagnostic or drug effect. This increases cost and diminishes safety, as well as presenting solubility problems (increased cross-linking decreases solubility). The amount of tissue receptor also limits the number of dextran molecules that can bind to the receptor and enter the cells. The resulting low density of drug or diagnostic agent cannot deliver an adequate amount to produce the desired effect.

The invention solves these problems by providing a carrier-molecule with a sufficiently high density of attachment site "leashes".

The invention also overcomes the shortcoming of low attachment flexibility provided by other schemes, e.g., Gedda et al.(1996), *Bioconj. Chem.* 7:584–591, and Holmberg et al. (1993), *Bioconj. Chem.* 4:570–573, describing non-amino-terminated leash systems. The lack of flexibility within the prior art techniques limits the range of possible applications. The invention avoids such limitations, thus providing for a wider range of applications.

REFERENCE

Albertini J J, Lyman G H, Cox C, Yeatman T, Balducci L, Ku N, Shivers S, Berman C, Well K, Rapaport D, Shons A, Horton J, Greenberg H, Nicosia S, Clark R, Cantor A, Reintgen D S. Lymphatic mapping and sentinel node biopsy in the patient with breast cancer. *JAMA* 276:1818–1822 (1996). Armitage F E, Richardson D E, Li KCP. Polymeric contrast agents for magnetic resonance imaging: Synthesis and characterization of gadolinium diethylenetriamine-pentaacetic acid conjugated to polysaccharides. *Bioconj. Chem.* 1:365–374 (1990).

Capizzi R L. Protection of normal tissues from the cytotoxic effects of chemotherapy by amifostine (ethyol): clincial experiences. *Semin Oncol* 21 (S11):8-1), 5 (1994).

De Cicco C, Cremonesi M, Luini A, Bartolmei M, Grana C, Gennaro P, Galimberti V, Calza P, Viale G, Veronesi U, Paganelli G. Lymphoscintigaphy and radioguided biopsy of the sentinel axillary node in breast cancer. *J. Nucl. Med.* 39-2080–2084 (1998)

Douay L, Hu C, Giarratana M-C, Gorin N-C. Comparative effects of amifostine (ethyol) on normal hematopoietic stem cells versus human leukemic cells during ex vivo purging in autologous bone marrow transplants. *Semin Oncol* 21(S11):16–20 (1994).

Dubois M. Colorimetric method for determination of sugars and related substances. *Anal. Chem.* 28:350–356 (1956).

Fields R C. The rapid determination of amino groups with TNBS, *Meth. Enzymol.* 25; 464–468 (1972).

Glass E C, Essner R, Giuliano A, Morton D L. Comparative efficacy of three lymphoscintigraphic agents. *JNuclMed*36:199P (1995).

Guiliano A E, Kirgan D M, Guenther J M, Morton D L. Lymphatic mapping and sentinel lymphadenectomy for breast cancer. *Ann. Surg.* 220:391–401 (1994).

Guiliano A-E. Axillary node mapping for breast cancer. Presented at the 48th Annual Symposium of the Society of Surgical Oncology, March 23–25, Boston, Mass. (1995).

Gedda L, Olsson P, Ponten J, Carlsson J. Development and in vitro studies of epidermal growth factor-dextran conjugates for neutron capture therapy. *Bioconj Chem* 7:584–591 (1996).

Grist T M, Korosec F R, Peters D C, Witte S, Walovitch R C, Dolan R P, Bridson W E, Yucel E K, Mistretta Calif. Steady-state and dynamic MR angiography with MS-35: initial experience in humans. *Radiology* 207:539–544.

Henze E, Schelbert H R, Collins J D, Najafi A, Barrio J R, Bennett L R. Lymphoscintigraphy with Tc-99m-labeled dextran. *J. Nucl. Med* 23:923–929 (1982).

Holmberg A, Meurling L. Preparation of sulfhydrylborane-dextran conjugates for boron neutron capture therapy. *Bioconjugate Chem* 4:570–573 (1993).

Krag D N, Weaver J C, Alex J C, Fairbank J T. Surgical resection and radiolocalization of the sentinel lymph node in breast cancer using a gamma probe. *J. Surg. Oncol.* 2:335–340 (1993).

Krag, D N. Gamma-probe-guided resection of axillary sentinel nodes. Presented at the 48th annual symposium of the Society of Surgical Oncology, March 23–25, Boston, Mass. (1995).

Krag, D N, Weaver D, Ashikaga T, Moffat F, Klimberg V S, Shriver C, Feldman S, Kusminsky R, Gadd M, Kuhn J, Harlow S, Beitsch P. The sentinel node in breast cancer—a multicenter validation study. *N Eng. J. Med.* 339:941–946 (1998).

Krejcarek., G E, Tucker K L. Covalent attachment of chelating groups to macromolecules. *Biochem. Biophys. Res. Commun.* 77:581–583 (1977).

Krinick N L, Rihova B, Lnbrich K, Strohalm J, Kopecek J., Synthesis of N-(2-hydroxypropyl)methacrylamide copolymer-anti-Thy 1.2 antibody-chlorin e6 conjugates and a preliminary study of their photodynamic effect on mouse splenocytes in vitro. *Makromol. Chem.* 191:839–856 (1990).

Lee Y C. Neoglycoconjugates: General Considerations, In Neoglycoconjugates: *Preparation and applications*. Lee Y C and Lee R T Eds. Academic Press, San Diego (1994).

Molteni L, Dextrans as drug carriers. In: Gregoriadis G, ed. *Drug carriers in biology and medicine.* San Diego, Academic Press; 107–125 (1979).

Morton D L, Wen D-R, Wong J H, Economou J S, Cagle L A, Storm K, Foshag L J, Cochran A J. Technical details of intraoperative lymphatic mapping for early stage melanoma. *Arch Surg* 127:392–299 (1992).

Phillips T L. Sensitizers and protectors in clinical oncology. *Semin Oncol* 8:67–82, (1881).

Rasey J S, Spence A M, Badger C C, Krohn K A, Vera D R, Livesey J C. Specific protection of different normal tissues. *Pharmac Ther* 39:33–43, (1988).

Rebizak R, Schaefer M, Dellacherie T., Polymeric conjugates of Gd 31 Diethylenetriaminepentaactic acid and dextran. 1. Synthesis, characterization, and paramagnetic properties. *Bioconj Chem* 8:605–610.

Rebizak R (1998), Schaefer M, Dellacherie P. Polymeric conjugates of Gd-Diethylenetriaminepentaactic acid and dextran. 2. Influence of spacer arm length and conjugate molecular mass on the paramagnetic properties and some biological parameters. *Bioconj. Chem.* 9:94–99 (1997).

Saha S (1998), Nora D, Espinosa M, Gauthier J, Morrison A, Rohatgi C, Dorman S, Jones T, Singh T, Arora M, Ganatra B K, Desa D. Diagnostic and therapeutic implications of sentinel node mapping in colorectal cancer: a Prospective study. *J Surg Oncol* 69:183.

Seymour L W. Passive tumor targeting of soluble macromolecules and drug conjugates. *Critical Reviews of Therapeutic Drug Carrier Systems* 9:135–187 (1992).

Sieving P F, Watson A D, Rocklage S M. Preparation and characterization of paramagnetic polychelates and their conjugates. *Bioconj. Chem.* 1:65–71, (1990).

Slingluff C L, Stidham K R, Ricci W M, Stanley W E, Seigler H F. Surgical management of regional lymph nodes in patients with melanoma: experience with 4682 patients. *Ann Surg* 219:120–130 (1994).

Snyder W S (1975), Ford M R, Warner G G et al. *'S' Absorbed Dose per Unit Cumulative Activity for Selected Radionuclides and Organs, MIRD Pamphlet No. 11.* New York Society of Nuclear Medicine, 1975.

Stadalnik R C, Vera D R, Woodle E S. Trudeau W L, Porter B A, Ward R E, Krohn K A, O'Grady L F. Technet-99m NGA functional imaging: preliminary clinical experience. *J. Nucl. Med* 26:1233–1224 (1985).

Steer C J, Ashwell G. Receptor-mediated endocytosis: Mechanisms, biologic function, and molecular properties. In: *Hepatology. A Textbook of liver Disease.* (2nd Ed.) Zakim D, Boyer T D, eds. W. B. Saunders, Philadelphia (1990).

Tomalia D A, Baker H, Deward J, et al. A new class of polymers: starburst-dendritic macromolecules. *Polymer J* 17:117–132 (1985).

Uren R F, Howman-Giles R B, Thompson J F, Malouf D, Ramsey-Stewart G, Niesche F W, Renwick, S B. Mammary lymphoscintigraphy in breast cancer. *J. Nucl. Med.* 1995 36:1775–1780 (1995).

Vera D R, Stadalnik R C, Krohn K A. Technetium-99m galactosyl-neoglycoalbumin: preparation and preclinical studies. *J. Nucl. Med* 26:1157–1167 (1985).

Vera D R, Buonocore M I H, Wisner E R, Katzberg R W, Stadalnik R C. A molecular receptor-binding contrast agent for magnetic resonance imaging of the liver. *Acad. Radiol.* 2:497–596 (1995).

Vera D R, Wisner E R, Stadalnik R C. Sentinel node imaging via a nonparticulate receptor-binding radiotracer. *J. Nucl. Med* 38:530–535 (1997).

Veronesi U, Paganelli G, Galimberti V, Viale G, Zurrida S, Bedoni M, Costa A, de Cicco C, Geraghty J G, Luini A, Sacchini V, Veronesi P. Sentinel-node biopsy to avoid axillary dissection in breast with clinically negative lymph-nodes. *Lancet* 349:1864–1867 (1997).

All of the preceding references are herein incorporated by reference.

Although exemplary embodiments of the invention have been described above by way of example only, it will be understood by those skilled in the field that modifications may be made to the disclosed embodiments without departing from the scope of the invention, which is defined by the appended claims.

I claim:

1. A carrier molecule comprising:
 a backbone, wherein said backbone is dextran;
 wherein said backbone having affixed thereto a plurality of groups having structure —O(CH$_2$)$_3$S(CH$_2$)$_2$NH$_2$;
 wherein said carrier is water soluble, non-toxic to humans and essentially cross-link free; and
 comprises at least one additional chemical group conjugated to the amino group of at least one said groups having the structure —O(CH$_2$)$_3$S(CH$_2$)$_2$NH$_2$.

2. The molecule of claim 1 produced by the reaction of an allyl group with aminoethanethiol.

3. The molecule of claim 1 wherein said at least one additional chemical group is selected from the group consisting of chelators, receptor ligands, enzymatic substrates, nucleic acids, peptides, polysaccharides, radiosensitizers, radioprotectors, antiviral agents and dyes.

4. The molecule of claim 3 wherein said at least one additional group is a chelator selected from the group consisting of tetraazacyclododecanetetraacetic acid (DOTA), mercaptoacetylglycylglycyl-glycine (MAG3), and diethylenetriamine pentaacetic acid (DTPA).

5. The molecule of claim 3 wherein said at least one additional group is a chelator capable of binding an atom selected from the group consisting of radioactive atoms, absorbing elements, and paramagnetic atoms.

6. The molecule of claim 5 wherein said molecule is useful for sentinel node imaging.

7. The molecule of claim 5 wherein said chelator is bound to gadolinium.

8. The molecule of claim 5 wherein said chelator is bound to ytterbium.

9. The molecule of claim 5 wherein said chelator is bound to Technetium-99m (Tc-99m).

10. The molecule of claim 5 wherein said chelator is bound to indium.

11. The molecule of claim 3 wherein said at least one additional group is a receptor ligand selected from the group consisting of mannose, galactose, monosaccharides, polysaccharides and peptides.

12. A magnetic resonance imaging (MRI) agent synthesized from the molecule of claim 1.

13. A computed tomography (CT) agent synthesized from the molecule of claim 1.

14. A method of producing a substantially cross-link-free carrier molecule having a plurality of amino terminated leashes, comprising:
 providing a backbone molecule having a plurality of hydroxyl groups, allylating at least a portion of said hydroxyl groups on said backbone molecule to produce an allyl derivative of said backbone;
 reacting said allyl groups of said allyl derivative with a compound comprising an amino terminus and a second terminus, said second terminus reactive with said allyl groups of said allyl derivative;
 reacting said allyl derivative with said compound to produce a substantially cross-link-free carrier molecule having a plurality of amino terminated leashes wherein each leash consists of —O(CH$_2$)$_3$S(CH$_2$)$_2$NH$_2$; and
 wherein each leash comprises at least one additional chemical group conjugated to an amino group of each leash.

15. The method of claim 14 wherein said compound is aminoethanethiol.

16. The method of claim 15 further comprising conjugating said amino terminated leashes with at least one member selected from the group consisting of chelators, receptor ligands, enzymatic substrates, nucleic acids, peptides, polysaccharides, monosaccharides, radiosensitizers, radioprotectors, and dyes.

17. The method of claim 16 wherein said at least one member is a chelator selected from the group consisting of DOTA, MAG3, and DTPA, and wherein said receptor ligand is selected from the group consisting of mannose, galactose, monosaccharides, polysaccharides and peptides.

18. The method of claim 17 further comprising adding an atom having an affinity for chelators, said atom selected from the group consisting of radioactive atoms, absorbing elements, and paramagnetic atoms.

19. The method of claim 18 further comprising using said conjugated substantially cross-link-free carrier molecule in a diagnostic procedure.

20. The method of claim 19 wherein said diagnostic procedure is sentinel node imaging.

21. The method of claim 16 further comprising the use of said conjugated substantially cross-link-free carrier molecule in a therapeutic application.

22. An agent synthesized using the method of claim 21 wherein said backbone or backbone molecule is dextran.

23. An MRI agent synthesized using the method of claim 14.

24. A CT agent synthesized using the method of claim 14.

25. A sentinel node detection agent made according to the method of claim 14 and further comprising a receptor substrate, a chelator, and a radioactive atom.

26. The sentinel node detection agent of claim 25 wherein said chelator is selected from the group consisting of DOTA, DTPA and MAG3.

27. The sentinel node detection agent of claim 25 wherein said receptor substrate is mannose.

28. The sentinel node detection agent of claim 27 wherein said radioactive atom is Tc-99m and said chelator is selected from the group consisting of DOTA, DTPA and MAG3.

29. The sentinel node detection agent of claim 25 wherein said backbone is a polysaccharide.

30. The sentinel node detection agent of claim 29 wherein said polysaccharide is a dextran.

31. The molecule of claim 5 wherein said chelator is bound to dysprosium.

* * * * *